(12) United States Patent
Baley et al.

(10) Patent No.: US 9,681,616 B2
(45) Date of Patent: *Jun. 20, 2017

(54) METHOD TO IDENTIFY ASIAN SOYBEAN RUST RESISTANCE QUANTITATIVE TRAIT LOCI IN SOYBEAN AND COMPOSITIONS THEREOF

(71) Applicant: Monsanto Technology LLC, St. Louis, MO (US)

(72) Inventors: George J. Baley, Webster Groves, MO (US); Vergel C. Concibido, Maryland Heights, MO (US); Bradley J. La Vallee, Clarkson Valley, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/093,686

(22) Filed: Apr. 7, 2016

(65) Prior Publication Data

US 2016/0212955 A1 Jul. 28, 2016

Related U.S. Application Data

(63) Continuation of application No. 14/553,465, filed on Nov. 25, 2014, now Pat. No. 9,332,698, which is a continuation of application No. 14/313,228, filed on Jun. 24, 2014, now Pat. No. 8,921,645, which is a continuation of application No. 14/157,176, filed on Jan. 16, 2014, now Pat. No. 8,796,503, which is a continuation of application No. 12/988,424, filed as application No. PCT/US2009/041390 on Apr. 22, 2009, now Pat. No. 8,669,414.

(60) Provisional application No. 61/047,479, filed on Apr. 24, 2008.

(51) Int. Cl.
| | |
|---|---|
| *A01H 1/02* | (2006.01) |
| *A01H 4/00* | (2006.01) |
| *A01H 5/10* | (2006.01) |
| *C12Q 1/68* | (2006.01) |
| *A01H 1/04* | (2006.01) |

(52) U.S. Cl.
CPC .............. *A01H 1/02* (2013.01); *A01H 1/04* (2013.01); *A01H 4/00* (2013.01); *A01H 5/10* (2013.01); *C12Q 1/6895* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 4,937,970 A | 7/1990 | Guan et al. |
|---|---|---|
| 7,097,975 B1 | 8/2006 | Frederick |
| 7,994,395 B2 | 8/2011 | Baley et al. |
| 2004/0031072 A1 | 2/2004 | La Rosa et al. |
| 2006/0041955 A1 | 2/2006 | Godwin et al. |
| 2006/0288444 A1 | 12/2006 | McCarroll et al. |
| 2009/0307799 A1 | 12/2009 | Baley et al. |

FOREIGN PATENT DOCUMENTS

WO     WO 2008/054546 A2     5/2008

OTHER PUBLICATIONS

"Soybean Genetic Resources and Genetic Enhancement White Paper," Jan. 2000 (9 pages), in U.S. Appl. No. 14/553,465.
Alan et al., "Sensitivity of Bacterial and Fungal Plant Pathogens to the Lytic Peptides, MSI-99, Magainin II, and CecripinB," *MPMI*, 15(7):701-708 (2002), in U.S. Appl. No. 14/553,465.
Anderson et al., "Statistical Procedures for Assessment of Resistance in a Multiple Foliar Disease Complex of Peanut," *Phytopathology*, 80(12):1451-1459 (1990), in U.S. Appl. No. 14/553,465.
Arahana et al., "Identification of QTLs for Resistance to *Sclerotinia sclerotiorum* in Soybean," *Crop Science*, 41:180-188 (2001), in U.S. Appl. No. 14/553,465.
Banyal et al., "Resistance of pea genotypes in relation to sporulation by *Erysiphe pisi*," *Crop Protection*, 16(1):51-55 (1997), in U.S. Appl. No. 14/553,465.
Bhattacharyya et al., "Expression of gene-specific and age-related resistance and the accumulation of glyceollin in soybean leaves infected with *Phytophthora megasperma* f. sp. Glycinea," *Physiological and Molecular Plant Pathology*, 29:105-113 (1986), in U.S. Appl. No. 14/553,465.
Brogin et al., "Molecular mapping of a gene conferring resistance to soybean rust," Abstracts of Contributed Papers from the VII World Soybean Research Conference, p. 318 (2004), in U.S. Appl. No. 14/553,465.
Brogin, "Mapeamento de Genes de Resistencia a Ferrugem e de QTLs Envolvidos na Resistencia à Septoriose em Soja," Univesidade de Sao Paulo, pp. 13-45 (2005), in U.S. Appl. No. 14/553,465.
Burdon et al., "Evaluation of Australian Native Species of *Glycine* for Resistance to Soybean Rust," *Plant Disease*, 65(1):44-45 (1981), in U.S. Appl. No. 14/553,465.
Bussey et al., "A Leaf Disk Assay for Detecting Resistance to Early Blight Caused by *Alternaria solani* in Juvenile Potato Plants," *Plant Disease*, 75(4):385-390 (1991), in U.S. Appl. No. 14/553,465.

(Continued)

*Primary Examiner* — Brent Page
*Assistant Examiner* — Jared Shapiro
(74) *Attorney, Agent, or Firm* — Arnold & Porter Kaye Scholer; Lawrence M. Lavin, Jr.; David Marsh

(57) ABSTRACT

The present invention is in the field of plant breeding and disease resistance. More specifically, the invention includes a method for breeding soybean plants containing quantitative trait loci that are associated with resistance to Asian Soybean Rust (ASR), a fungal disease associated with *Phakopsora* spp. The invention further includes germplasm and the use of germplasm containing quantitative trait loci (QTL) conferring disease resistance for introgression into elite germplasm in a breeding program for resistance to ASR.

7 Claims, 3 Drawing Sheets

(56) References Cited

OTHER PUBLICATIONS

Chang et al., "Two Additional Loci Underlying Durable Field Resistance to Soybean Sudden Death Syndrome (SDS)," *Crop Science*, 36:1684-1688 (1996), in U.S. Appl. No. 14/553,465.
Chen et al., "Two Convenient Methods to Evaluate Soybean for Resistance to *Sclerotinia sclerotiorum*," *Plant Disease*, 89(12):1268-1272 (2005), in U.S. Appl. No. 14/553,465.
Cline et al., "Methods for Evaluating Soybean Cultivars for Resistance to *Sclerotinia sclerotiorum*," *Plant Disease*, 67(7):784-786 (1983), in U.S. Appl. No. 14/553,465.
Collard et al., "An introduction to markers, quantitative trait loci (QTL) mapping and marker-assisted selection for crop improvement: The basic concepts," *Euphytica*, 142:169-196 (2005), in U.S. Appl. No. 12/988,424.
Cregan et al., "An Integrated Genetic Linkage Map of the Soybean Genome," *Crop Sci.*, 39:1464-1490 (1999), in U.S. Appl. No. 14/553,465.
Ding et al., "A putative IgG-binding 65 kDa adhesin involved in adhesion and infection of soybeans by *Phytophthora megasperma* f.sp. *glycinea*," *Physiological and Molecular Plant Pathology*, 44:363-378 (1994), in U.S. Appl. No. 14/553,465.
Dowkiw et al., "Partial Resistance to *Melampsora larici-populina* Leaf Rust in Hybrid Poplars: Genetic Variability in Inoculated Excised Leaf Disk Bioassay and Relationship with Complete Resistance," *Phytopathology*, 93(4):421-427 (2003), in U.S. Appl. No. 14/553,465.
European Search Report issued Jun. 11, 2012, in European Patent Application No. 11 1945 11.9, in U.S. Appl. No. 14/553,465.
European Search Report issued Jun. 13, 2012, in European Patent Application No. 11 194 514.3, in U.S. Appl. No. 14/553,465.
European Search Report issued Jun. 19, 2012, in European Patent Application No. 11 194 515.0, in U.S. Appl. No. 14/553,465.
Examination Report dated Apr. 13, 2011, in European Patent Application No. 07 867 133.6, 7 pages, in U.S. Appl. No. 14/553,465.
Fehr et al., "Stage of Development Descriptions for Soybeans, *Glycine Max* (L.) Merrill," *Crop Science*, 11:929-931 (1971), in U.S. Appl. No. 14/553,465.
Frederick et al., "Polymerase Chain Reaction Assays for the Detection and Discrimination of the Soybean Rust Pathogens *Phakopsora pachyrhizi* and *P. meibomiae*," *Phytopathology*, 92(2):217-227 (2002), in U.S. Appl. No. 14/553,465.
Gupta et al., "Single nucleotide polymorphisms: A new paradigm for molecular marker technology and DNA polymorphism detection with emphasis on their use in plants," *Current Science*, 80(4):524-535 (2001), in U.S. Appl. No. 14/553,465.
Hartman et al., "Breeding for Resistance to Soybean Rust," *Plant Disease*, 89(6):664-666 (2005), in U.S. Appl. No. 14/553,465.
Hartwig et al., "Relationships Among Three Genes Conferring Specific Resistance to Rust in Soybeans," *Crop Science*, 23:237-239 (1983), in U.S. Appl. No. 14/553,465.
Herath et al., "Evaluating faba beans for rust resistance using detached leaves," *Euphytica*, 117:47-57 (2001), in U.S. Appl. No. 14/553,465.
Hershman, "Bacterial Leaf Blights," Soybean Disease Atlas, 2nd ed., P.D. Colyer (ed.), Associated Printing Professionals, Inc., 2 pages (1989), in U.S. Appl. No. 14/553,465.
Hsieh et al., "Leaf-disk method for assessment of disease severity of lily leaf blight caused by *Botrytis elliptica*," *Plant Pathology Bulletin*, 10:37-44 (2001), in U.S. Appl. No. 14/553,465.
Hyten et al., "Map Location of the *Rpp1* Locus That Confers Resistance to Soybean Rust in Soybean," *Crop Science* 47:837-840 (2007), in U.S. Appl. No. 12/988,424.
International Search Report issued Jan. 16, 2009, in International Application No. PCT/US2007/012363, in U.S. Appl. No. 14/553,465.
Kasuga et al., "High Resolution Genetic and Physical Mapping of Molecular Markers Linked to the *Phytophthora* Resistance Gene *Rps1*-in Soybean," *Molecular Plant-Microbe Interactions*, 10(9):1035-1044 (1997), in U.S. Appl. No. 14/553,465.
Kim et al., "Inheritance of Partial Resistance to Sclerotinia Stem Rot in Soybean", *Crop Science*, 40:55-61 (2000), in U.S. Appl. No. 14/553,465.
Kim et al., "Reaction of Soybean Cultivars to Sclerotinia Stem Rot in Field, Greenhouse, and Laboratory Evaluations," *Crop Science*, 40:665-669 (2000), in U.S. Appl. No. 14/553,465.
Kull et al., "Evaluation of Resistance Screening Methods for Sclerotinia Stem Rot of Soybean and Dry Bean," *Plant Disease*, 87:1471-1476 (2003), in U.S. Appl. No. 14/553,465.
Lebeda, "Screening of Wild *Cucumis* Species for Resistance to Cucumber Powdery Mildew (*Erysiphe cichoracearum* and *Sphaerotheca fuliginea*)," *Scientia Horticulturae*, 24:241-249 (1984), in U.S. Appl. No. 14/553,465.
Lewers et al., "Detection of linked QTL for soybean brown stem rot resistance in 'BSR 101' as expressed in a growth chamber environment," *Molecular Breeding*, 5(1):33-42 (1999), in U.S. Appl. No. 14/553,465.
Maxwell et al., "Effects of Water Stress on Colonization of Poplar Stems and Excised Leaf Disks by *Septoria musiva*," *Ecology and Population Biology*, 87(4):381-388 (1997), in U.S. Appl. No. 14/553,465.
McLean et al., "Inheritance of resistance to rust (*Phakopsora pachyrhizi*) in soybeans," *Australian Journal f Agricultural Research*, 31(5):951-956 (1980), in U.S. Appl. No. 14/553,465.
Meksem et al., "Conversion of AFLP bands into high-throughput DNA markers," *Mol. Genet. Genomics*, 265:207-2014 (2001), in U.S. Appl. No. 14/553,465.
Melching et al., "Effect of plant and leaf age on susceptability of soybean to soybean rust," Canadian Journal of Plant Pathology 10:30-35, 1998, in U.S. Appl. No. 14/553,465.
Mieslerová et al., "Variation in Response of Wild *Lycopersicon* and *Solanum* spp. against Tomato Powdery Mildew (*Oidium lycopersici*)," *J. Phytopathology*, 148:303-311 (2000), in U.S. Appl. No. 14/553,465.
Monteros et al., "Mapping and Confirmation of the 'Hyuuga' Red-Brown Lesion Resistance Gene for Asian Soybean Rust," *Crop Science*, 47:829-836 (2007), in U.S. Appl. No. 12/988,424.
NPGS Soybean Accession PI200492, deposited Apr. 15, 1952, in U.S. Appl. No. 14/553,465.
NPGS Soybean Accession PI368037, deposited Nov. 26, 1971, in U.S. Appl. No. 14/553,465.
Nuntapunt et al., "Soybean breeding for rust resistance in Thailand and extent of rust resistant cultivars used," Proceedings VII World Soybean Research Conference, pp. 423-430 (2004), in U.S. Appl. No. 14/553,465.
Orlandi et al., "Early physiological responses associated with race-specific recognition in soybean leaf tissue and cell suspensions treated with *Pseudomonas syringae* pv. *Glycinea*," *Physiological and Molecular Plant Pathology*, 40:173-180 (1992), in U.S. Appl. No. 14/553,465.
Owens et al., "Genotypic Variability of Soybean Response to *Agrobacterium* Strains Harboring the Ti or Ri Plasmids," *Plant Physiol.*, 77:87-94 (1985), in U.S. Appl. No. 14/553,465.
Partial International Search Report issued May 19, 2009, in International Application No. PCT/US2009/041390, in U.S. Appl. No. 12/988,424.
Paul et al., "Potential of Detached Soybean Leaves for Evaluation of Rust Resistance," Presented at Molecular and Cellular Biology of the Soybean Conference, 1 page (2006), in U.S. Appl. No. 14/553,465.
Phillips, "Fungal Leaf Spots," Soybean Disease Atlas, 2nd ed., P.D. Colyer (ed.), Associated Printing Professionals, Inc., 6 pages (1989), in U.S. Appl. No. 14/553,465.
Pratt, "Screening for Resistance to *Sclerotinia trifoliorum* in Alfalfa by Inoculation of Excised Leaf Tissue," *Phytopathology*, 86(9):923-928 (1996), in U.S. Appl. No. 14/553,465.
Reddy et al., "Screening for powdery mildew (*Erysiphae polygoni* DC.) resistance in mungbean (*Vigna radiata* (L.) Wilczek) using excised leaves," *Proc. Indian Acad. Sci. (Plant Sci.)*, 97(5):365-369 (1987), in U.S. Appl. No. 14/553,465.
Robertson et al., "Soybean Rust and Common Soybean Leaf Diseases," *PM 1989*, Iowa State University, 4 pages (2008), in U.S. Appl. No. 14/553,465.

(56) References Cited

OTHER PUBLICATIONS

Ruhl, "Crop Diseases in Corn, Soybean, and Wheat," Purdue University, 7 pages (2007) <http://www.btny.purdue.edu/extension/pathology/cropdiseases/soybean/Soybean.html>, in U.S. Appl. No. 14/553,465.
Shanmugasundaram et al., "Breeding for soybean rust resistance in Taiwan," *Proceedings of the VII World Soybean Research Conference*, pp. 456-462 (2004), in U.S. Appl. No. 14/553,465.
Sharma et al., "Identification of soybean strains resistant to *Xanthonomas campestris* pv. *Glycines*," *Euphytica*, 67:95-99 (1993), in U.S. Appl. No. 14/553,465.
Sillero et al., "Screening techniques and sources of resistance to rusts and mildews in grain legumes," *Euphytica*, 147:255-272 (2006), in U.S. Appl. No. 14/553,465.
Silva et al., "Molecular mapping of two loci that confer resistance to Asian rust in soybean," *Theor Appl Genet*, 117:57-63 (2008), in U.S. Appl. No. 12/988,424.
Singh et al., "Sources of Field Resistance to Rust and Yellow Mosaic Diseases of Soybean," *Indian Journal of Genetics & Plant Breeding*, 34(3):400-404 (1974), in U.S. Appl. No. 14/553,465.
Smit, "Proceedings of Workshop on Soybean Rust (*Phakopsora pachyrhizi*)," *ARC-Grain Crops Institute*, 40 pages (1998), in U.S. Appl. No. 14/553,465.
Sweets et al., "Soybean Rust," *MU Guide, Bulletin G4442*, University of Missouri-Columbia, 6 pages (2004), in U.S. Appl. No. 14/553,465.
Twizeyimana et al., "A detached leaf method to evaluate soybean for resistance to rust," National Soybean Rust Symposium, 1 page(2006), in U.S. Appl. No. 14/553,465.
Twizeyimana et al., "Comparison of Field, Greenhouse, and Detached-Leaf Evaluations of Soybean Germplasm for Resistance to *Phakopsora pachyrhizi*," *Plant Disease*, 91(9):1161-1169 (2007), in U.S. Appl. No. 14/553,465.
USDA, ARS, National Genetic Resources Program. Germplasm Resources Information Network—(GRIN). [Online Database] National Germplasm Resources Laboratory, Beltsville, Maryland (Apr. 5, 2013) <http://www.ars-grin.gov/cgi-bin/npgs/acc/display.pl?1169224>, in U.S. Appl. No. 14/553,465.
Vodkin et al., "II-D. Testing for DNA Markers Associated with Rust Resistance in Soybean," Proceedings of the Soybean Rust Workshop, National Soybean Research Laboratory Publication, 1:68 (1995), in U.S. Appl. No. 14/553,465.
Walters et al., "Induction of systemic resistance to rust in *Vicia faba* by phosphate and EDTA: effects of calcium," *Plant Pathology*, 41:444-448 (1992), in U.S. Appl. No. 14/553,465.
Wang et al., "Epidemiology of Soybean Rust and Breeding for Host Resistance," *Plant Protection Bulletin*, 34:109-124 (1992), in U.S. Appl. No. 14/553,465.
Ward et al., "Hypocotyl Reactions and Glyceollin in Soybeans Inoculated with Zoospores of *Physophthora megasperma* var. *sojae*," *Phytopathology*, 69(9):951-955 (1979), in U.S. Appl. No. 14/553,465.
Wegulo et al., "Soybean Cultivar Responses to *Sclerotinia sclerotiorum* in Field and Controlled Environment Studies," *Plant Disease*, 82(11):1264-1270 (1998), in U.S. Appl. No. 14/553,465.
Westman et al., "The potential for cross-taxa simple-sequence repeat (SSR) amplification between *Arabidopsis thaliana* L. and crop brassicas," *Theor Appl Genet*, 96:272-281 (1998), in U.S. Appl. No. 14/553,465.
Whitney, "Seedling Diseases," Soybean Disease Atlas, 2nd ed., P.D. Colyer (ed.), Associated Printing Professionals, Inc., 4 pages (1989), in U.S. Appl. No. 14/553,465.
Wynstra (ed.), The NSRL Bulletin, National Soybean Research Laboratory, University of Illinois, Urbana, IL, 2(3):5 (1995), in U.S. Appl. No. 14/553,465.
Xie et al., "A Leaf Inoculation Method for Detection of *Xanthomonas oryzae* pv. *oryzicola* from Rice Seed," *Plant Disease*, 82:1007-1011(1998), in U.S. Appl. No. 14/553,465.
Young, "QTL Mapping and Quantitative Disease Resistance in Plants," *Annu. Rev. Phytopathol.*, 34:479-501 (1996), in U.S. Appl. No. 12/988,424.

METHOD TO IDENTIFY ASIAN SOYBEAN RUST RESISTANCE QUANTITATIVE TRAIT LOCI IN SOYBEAN AND COMPOSITIONS THEREOF

CROSS-REFERENCE TO RELATED APPLICATIONS

This application is a continuation of U.S. application Ser. No. 14/553,465, filed Nov. 25, 2014, which is a continuation of U.S. application Ser. No. 14/313,228, filed Jun. 24, 2014 (now U.S. Pat. No. 8,921,645), which is a continuation of U.S. application Ser. No. 14/157,176, filed Jan. 16, 2014 (now U.S. Pat. No. 8,796,503), which is a continuation of U.S. application Ser. No. 12/988,424, filed Nov. 4, 2010 (now U.S. Pat. No. 8,669,414), which is a U.S. National Stage Application of PCT/US2009/041390, filed Apr. 22, 2009, which claims the benefit under 35 U.S.C. §119(e) of U.S. Provisional Application No. 61/047,479 filed 24 Apr. 2008. The entirety of each aforementioned application is hereby incorporated by reference.

INCORPORATION OF THE SEQUENCE LISTING

A sequence listing containing the file named "P30911US05_SEQ.txt" which is 25,863 bytes (measured in Microsoft Windows®) and created on Apr. 4, 2016, comprises 80 sequences, and is herein incorporated by reference in its entirety.

FIELD OF THE INVENTION

The present invention is in the field of plant breeding and disease resistance. More specifically, the invention includes a method for breeding soybean plants containing quantitative trait loci that are associated with resistance to Asian soybean rust disease (ASR) caused by *Phakopsora pachyrhizi* and *Phakopsora meibomiae*. The invention further includes germplasm, novel quantitative trait loci (QTL) conferring resistance to ASR, and methods for introgressing the novel QTL into elite germplasm in a breeding program for resistance to ASR.

BACKGROUND OF THE INVENTION

The soybean, *Glycine max* (L.) Merril, is one of the major economic crops grown worldwide as a primary source of vegetable oil and protein (Sinclair and Backman, *Compendium of Soybean Diseases,* 3$^{rd}$ Ed. APS Press, St. Paul, Minn., p. 106 (1989)). The growing demand for low cholesterol and high fiber diets has also increased soybean's importance as a health food.

Soybean yields in the United States are negatively affected each year by diseases. High yields per hectare are critical to a farmer's profit margin, especially during periods of low prices for soybean. The financial loss caused by soybean diseases is important to rural economies and to the economies of allied industries in urban areas. The effects of these losses are eventually felt throughout the soybean market worldwide.

Asian Soybean Rust (herein referred to as ASR) has been reported in the Eastern and Western Hemispheres. In the Eastern Hemisphere, ASR has been reported in Australia, China, India, Japan, Taiwan and Thailand. In the Western Hemisphere, ASR has been observed in Brazil, Columbia, Costa Rica and Puerto Rico. ASR can be a devastating disease, causing yield losses of up to 70 to 80% as reported in some fields in Taiwan. Plants that are heavily infected have fewer pods and smaller seeds that are of poor quality (Frederick et al., *Mycology* 92: 217-227 (2002)). ASR was first observed in the United States in Hawaii in 1994. ASR was later introduced into the continental United States in the fall of 2004, presumably as a consequence of tropical storm activity. Model predictions indicated that ASR had been widely dispersed throughout the southeastern United States, and subsequent field and laboratory observations confirmed this distribution.

Two species of fungi, *Phakopsora pachyrhizi* Sydow and *Phakopsora meibomiae* (Arthur) Arthur, cause ASR. Unlike other rusts, *P. pachyrhizi* and *P. meibomiae* infect an unusually broad range of plant species. *P. pachyrhizi* is known to naturally infect 31 species in 17 genera of legumes and 60 species in 26 other genera have been infected under controlled conditions. *P. meibomiae* naturally infects 42 species in 19 genera of legumes, and 18 additional species in 12 other genera have been artificially infected. Twenty-four plant species in 19 genera are hosts for both species (Frederick et al., *Mycology* 92: 217-227 (2002)).

Evaluating plants that could potentially contain QTL conferring resistance to ASR can be time consuming and require large amounts of biologically contained space. Culturing *P. pachyrhizi* requires the use of an approved biological containment hood. In addition, greenhouses and growth chambers used to grow plants for ASR resistance testing have to be constructed in a manner that prevents the accidental release of the organism, especially in locations in which the organism has still not yet been observed. Different cultures of *P. pachyrhizi* may possess different virulence factors. Over time, new strains of *P. pachyrhizi* may be introduced into the United States. The two principal hosts are yarn bean (*Pachyrhizus erosus* (L.) Urban) and cowpea (*Vigna unguiculata* (L.) Walp.), both found in Florida. One widespread naturalized host for *P. pachyrhizi* and *P. meibomiae* is kudzu (*Pueraria montana* (Lour.) Merr. var. *lobata* (Willd.) Maesen & S. M. Almeida ex Sanjappa & Predeep). Because kudzu is a common weed in the southeastern United States, it might serve as a continual source of inoculum. Both *P. pachyrhizi* and *P. meibomiae* are autoecious (no alternate hosts) and microcyclic (with uredinial and telial spore stages), with the obligate pathogens surviving and reproducing only on live hosts. Additional hosts can serve as over-wintering reservoirs for the pathogen, as well as build-up of inoculum. The pathogen is well adapted for long-distance dispersal, because the spores can be readily carried by the wind, making it an ideal means for introduction to new, rust-free regions. The primary means of dissemination are spores, which can be carried by wind or splashed rain.

Because different cultures of *P. pachyrhizi* may possess different virulence factors to known and suspected genes for resistance, it follows that different ASR resistance loci in the soybean genome may be expected to differ with respect to which strain(s) of *P. pachyrhizi* and or *P. meibomiae* they confer resistance against. Therefore, any breeding program designed to breed resistance into soybean against ASR will likely need to involve multifactorial resistance derived from different resistance loci in the soybean genome, in order to confer robust resistance against ASR despite changes in the *P. pachyrhizi* population. Also, breeding for soybean crops used in other geographic locations will require selecting resistance to the specific strains that affect those regions, in addition to providing those agronomic characteristics that are preferred by these farmers in that region. There is therefore strong motivation to identify novel ASR resistance loci in soybean, and to introgress desirable alleles into elite soybean germplasm. Methodology has been developed to evaluate plants that could potentially contain QTL conferring resistance to ASR (U.S. Patent Appl No. 20080166699).

SUMMARY OF THE INVENTION

The present invention provides a method for introgressing an allele into a soybean plant comprising: crossing at least one ASR resistant soybean plant with at least one other soybean plant to form a population; and screening the population with at least one nucleic acid marker from the group consisting of ASR resistance loci 14, 15 and 16, to determine if one or more soybean plants from the population contains at least one ASR resistance allele from the group consisting of ASR resistance alleles 1 through 8. In various embodiments, the at least one marker is located within 30 cM, 15 cM, 5 cM or 1 cM of the resistance allele, or within 1 Mb, 100 Kb or 1 Kb of the resistance allele.

In another aspect, the invention provides an elite soybean plant produced by: crossing at least one ASR resistant soybean plant with at least one other soybean plant to form a population; and screening the population with at least one nucleic acid marker from the group consisting of ASR resistance loci 14, 15 and 16, to determine if one or more soybean plants from the population contains at least one ASR resistance allele from the group consisting of ASR resistance alleles 1 through 8. In one embodiment, the elite soybean plant exhibits at least one transgenic trait. In a more particular embodiment, the at least one transgenic trait may be herbicide tolerance, increased yield, insect control, fungal disease resistance, virus resistance, nematode resistance, bacterial disease resistance, *mycoplasma* disease resistance, modified oils production, high oil production, high protein production, germination and seedling growth control, enhanced animal and human nutrition, low raffinose, environmental stress resistance, increased digestibility, improved processing traits, improved flavor, nitrogen fixation, hybrid seed production, reduced allergenicity or any combination thereof. In a yet more particular embodiment, herbicide tolerance may be conferred for glyphosate, dicamba, glufosinate, sulfonyl urea, bromoxynil, 2,4-Dichlorophenoxyacetic acid, norflurazon herbicides or any combination thereof. In yet another embodiment, the elite soybean plant exhibits at least partial resistance to at least one race of an ASR-inducing fungus and more particularly the ASR-inducing fungus may be *Phakopsora. pachyrhizi* or *P. meibomiae* or both.

The invention also provides a method of introgressing at least one ASR resistance allele into a soybean plant comprising the steps: crossing an ASR resistant soybean plant with a second soybean plant to form a population; screening the population with at least one nucleic acid marker selected from the group consisting of SEQ ID NO: 1 through 8 and SEQ ID NO: 73 through 80; and selecting from the population at least one soybean plant comprising at least one genotype corresponding to the ASR resistant soybean plant. In particular embodiments, the selected soybean plant exhibits a resistant reaction rating to ASR of no worse than about 3, or of no worse than about 2, as described herein. In a more particular embodiment, the method further comprises the step of assaying the selected soybean plant for resistance to an ASR inducing pathogen. In another particular embodiment, the genotype is determined by single base extension (SBE), allele-specific primer extension sequencing (ASPE), DNA sequencing, RNA sequencing, microarray-based analyses, universal PCR, allele specific extension, hybridization, mass spectrometry, ligation, extension-ligation, or Flap Endonuclease-mediated assays. In still more particular embodiments, the method further comprises the step of crossing the selected soybean plant to another soybean plant; and still further comprises the step of obtaining seed from the selected soybean plant. In yet another particular embodiment, the at least one soybean plant in the population is genotyped with respect to a soybean genomic DNA marker selected from the group consisting of SEQ ID NO: 1 and 2 and with respect to SEQ ID NO: 3.

In another aspect, the invention provides an elite soybean plant produced by: crossing an ASR resistant soybean plant with a second soybean plant to form a population; screening said population with at least one nucleic acid marker selected from the group consisting of SEQ ID NO: 1 through 8, and SEQ ID NO: 73 through 80; and selecting from said population one or more soybean plants comprising at least one genotype corresponding to the ASR resistant soybean plant. In one embodiment, the elite soybean plant exhibits at least one transgenic trait. In a more particular embodiment, the transgenic trait may be herbicide tolerance, increased yield, insect control, fungal disease resistance, virus resistance, nematode resistance, bacterial disease resistance, *mycoplasma* disease resistance, modified oils production, high oil production, high protein production, germination and seedling growth control, enhanced animal and human nutrition, low raffinose, environmental stress resistance, increased digestibility, improved processing traits, improved flavor, nitrogen fixation, hybrid seed production, reduced allergenicity or any combination thereof. In a yet more particular embodiment, herbicide tolerance may be conferred for glyphosate, dicamba, glufosinate, sulfonylurea, bromoxynil, 2,4-Dichlorophenoxyacetic acid, norflurazon herbicides or any combination thereof. In yet other embodiments, the elite soybean plant exhibits at least partial resistance to at least one race of an ASR-inducing fungus and more particularly the ASR-inducing fungus may be *Phakopsora pachyrhizi* or *Phakopsora meibomiae* or both.

The invention also provides a substantially purified nucleic acid molecule for the detection of loci related to ASR resistance, comprising a nucleic acid sequence selected from the group consisting of SEQ ID NO: 1 through SEQ ID NO: 80 and complements thereof.

Further, the invention provides an isolated nucleic acid molecule of at least 15, 16, 17, 18 or 20 nucleotides, having at least 90% identity to a sequence of the same length in either strand of soybean DNA that includes or is adjacent to a polymorphism, for detecting a molecular marker representing the polymorphism, wherein the molecular marker is selected from the group consisting of SEQ ID NO: 1 though 8. In another embodiment, the invention provides an isolated nucleic acid molecule of at least 15, 16, 17, 18 or 20 nucleotides, having at least 95%, or preferably 98%, or more preferably 99% or even 100% identity to a sequence of the same length in either strand of soybean DNA that includes or is adjacent to a polymorphism, for detecting a molecular marker representing the polymorphism, wherein the molecular marker is selected from the group consisting of SEQ ID NO: 1 though 8. In a particular embodiment, the isolated nucleic acid further comprises a detectable label or provides for incorporation of a detectable label. More particularly, the detectable label may be an isotope, a fluorophore, an oxidant, a reductant, a nucleotide or a hapten. In a yet particular embodiment, the detectable label may be added to the nucleic acid by a chemical reaction or incorporated by an enzymatic reaction. In another embodiment of the invention, the isolated nucleic acid hybridizes to at least one allele of the molecular marker under stringent hybridization conditions. In more particular embodiments, the molecular marker is SEQ ID NO: 1, 2, 3, 4, 5, 6, 7 or 8; and the isolated nucleic acid is an oligonucleotide that is at least 90% identical to provided probes corresponding to the particular molecular marker, which are respectively: SEQ ID NO: 25 and 26, 27 and 28, 29 and 30, 31 and 32, 33 and 34, 35 and 36, 37 and 38, or 39 and 40.

The invention also provides a set of oligonucleotides comprising: a pair of oligonucleotide primers, each at least 12 contiguous nucleotides long, that permit PCR amplification of a DNA segment comprising or contained within a molecular marker selected from the group consisting of SEQ ID NO: 1 through 8; and at least one detector oligonucleotide that permits detection of a polymorphism in the amplified segment, wherein the sequence of the detector oligonucleotide is at least 95 percent identical to a sequence of the same number of consecutive nucleotides in either strand of a segment of soybean DNA that include or are adjacent to the polymorphism. In one embodiment, the detector oligonucleotide comprises at least 12 nucleotides and either provides for incorporation of a detectable label or further comprises a detectable label. In a more particular embodiment, the detectable label is selected from the group consisting of an isotope, a fluorophore, an oxidant, a reductant, a nucleotide and a hapten. In another embodiment, the detector oligonucleotide and said oligonucleotide primers hybridize to at least one allele of the molecular marker under stringent hybridization conditions. Yet other embodiments comprise a second detector oligonucleotide capable of detecting a distinct second polymorphism of the molecular marker or a distinct allele of the same polymorphism. In yet more particular embodiments, the molecular marker is SEQ ID NO: 1, 2, 3, 4, 5, 6, 7 or 8; and the oligonucleotide primers are at least 90% identical to provided primers corresponding to the particular molecular marker, which are respectively: SEQ ID NO: 9 and 10, 11 and 12, 13 and 14, 15 and 16, 17 and 18, 19 and 20, 21 and 22, or 23 and 24; and the detector oligonucleotide comprises a nucleic acid that is at least 90% identical to provided probes corresponding to the particular molecular marker, which are respectively: SEQ ID NO: 25 and 26, 27 and 28, 29 and 30, 31 and 32, 33 and 34, 35 and 36, 37 and 38, or 39 and 40.

The invention also provides a method of introgressing an allele into a soybean plant comprising: providing a population of soybean plants; genotyping at least one soybean plant in the population with respect to a soybean genomic nucleic acid marker selected from the group SEQ ID NO: 1 to 8 and SEQ ID NO: 73 to 80; and selecting from the population one or more soybean plants comprising an allele associated with ASR resistance, wherein said ASR resistance allele is selected from the group consisting of SEQ ID NO: 73 through SEQ ID NO: 80. In one embodiment, providing a population comprises crossing an ASR resistant soybean plant with a second soybean plant to form a population. In another embodiment, the selected one or more soybean plants exhibit increased grain yield in the presence of ASR as compared to soybean plants lacking ASR resistance alleles. More particularly, increased grain yield may be at least 0.5 Bu/A, at least 1.0 Bu/A, or at least 1.5 Bu/A in the presence of ASR as compared to soybean plants lacking ASR resistance alleles.

BRIEF DESCRIPTION OF NUCLEIC ACID SEQUENCES

SEQ ID NO: 1 is a genomic sequence derived from *Glycine max* associated with ASR resistance locus 14.
SEQ ID NO: 2 is a genomic sequence derived from *Glycine max* associated with ASR resistance locus 14.
SEQ ID NO: 3 is a genomic sequence derived from *Glycine max* associated with ASR resistance locus 14.
SEQ ID NO: 4 is a genomic sequence derived from *Glycine max* associated with ASR resistance locus 15.
SEQ ID NO: 5 is a genomic sequence derived from *Glycine max* associated with ASR resistance locus 15.
SEQ ID NO: 6 is a genomic sequence derived from *Glycine max* associated with ASR resistance locus 15.
SEQ ID NO: 7 is a genomic sequence derived from *Glycine max* associated with ASR resistance locus 16.
SEQ ID NO: 8 is a genomic sequence derived from *Glycine max* associated with ASR resistance locus 16.
SEQ ID NO: 9 is a forward PCR primer for the amplification of SEQ ID NO: 1.
SEQ ID NO: 10 is a reverse PCR primer for the amplification of SEQ ID NO: 1.
SEQ ID NO: 11 is a forward PCR primer for the amplification of SEQ ID NO: 2.
SEQ ID NO: 12 is a reverse PCR primer for the amplification of SEQ ID NO: 2.
SEQ ID NO: 13 is a forward PCR primer for the amplification of SEQ ID NO: 3.
SEQ ID NO: 14 is a reverse PCR primer for the amplification of SEQ ID NO: 3.
SEQ ID NO: 15 is a forward PCR primer for the amplification of SEQ ID NO: 4.
SEQ ID NO: 16 is a reverse PCR primer for the amplification of SEQ ID NO: 4.
SEQ ID NO: 17 is a forward PCR primer for the amplification of SEQ ID NO: 5.
SEQ ID NO: 18 is a reverse PCR primer for the amplification of SEQ ID NO: 5.
SEQ ID NO: 19 is a forward PCR primer for the amplification of SEQ ID NO: 6.
SEQ ID NO: 20 is a reverse PCR primer for the amplification of SEQ ID NO: 6.
SEQ ID NO: 21 is a forward PCR primer for the amplification of SEQ ID NO: 7.
SEQ ID NO: 22 is a reverse PCR primer for the amplification of SEQ ID NO: 7.
SEQ ID NO: 23 is a forward PCR primer for the amplification of SEQ ID NO: 8.
SEQ ID NO: 24 is a reverse PCR primer for the amplification of SEQ ID NO: 8.
SEQ ID NO: 25 is a probe for the detection of the SNP of SEQ ID NO: 1.
SEQ ID NO: 26 is a probe for the detection of the SNP of SEQ ID NO: 1.
SEQ ID NO: 27 is a probe for the detection of the SNP of SEQ ID NO: 2.
SEQ ID NO: 28 is a probe for the detection of the SNP of SEQ ID NO: 2.
SEQ ID NO: 29 is a probe for the detection of the SNP of SEQ ID NO: 3.
SEQ ID NO: 30 is a probe for the detection of the SNP of SEQ ID NO: 3.
SEQ ID NO: 31 is a probe for the detection of the SNP of SEQ ID NO: 4.
SEQ ID NO: 32 is a probe for the detection of the SNP of SEQ ID NO: 4.

SEQ ID NO: 33 is a probe for the detection of the SNP of SEQ ID NO: 5.

SEQ ID NO: 34 is a probe for the detection of the SNP of SEQ ID NO: 5.

SEQ ID NO: 35 is a probe for the detection of the SNP of SEQ ID NO: 6.

SEQ ID NO: 36 is a probe for the detection of the SNP of SEQ ID NO: 6.

SEQ ID NO: 37 is a probe for the detection of the SNP of SEQ ID NO: 7.

SEQ ID NO: 38 is a probe for the detection of the SNP of SEQ ID NO: 7.

SEQ ID NO: 39 is a probe for the detection of the SNP of SEQ ID NO: 8.

SEQ ID NO: 40 is a probe for the detection of the SNP of SEQ ID NO: 8.

SEQ ID NO: 41 is a hybridization probe for an ASR resistance allele corresponding to SEQ ID NO: 1.

SEQ ID NO: 42 is a hybridization probe for an ASR susceptibility allele corresponding to SEQ ID NO: 1.

SEQ ID NO: 43 is a hybridization probe for an ASR resistance allele corresponding to SEQ ID NO: 2.

SEQ ID NO: 44 is a hybridization probe for an ASR susceptibility allele corresponding to SEQ ID NO: 2.

SEQ ID NO: 45 is a hybridization probe for an ASR resistance allele corresponding to SEQ ID NO: 3.

SEQ ID NO: 46 is a hybridization probe for an ASR susceptibility allele corresponding to SEQ ID NO: 3.

SEQ ID NO: 47 is a hybridization probe for an ASR resistance allele corresponding to SEQ ID NO: 4.

SEQ ID NO: 48 is a hybridization probe for an ASR susceptibility allele corresponding to SEQ ID NO: 4.

SEQ ID NO: 49 is a hybridization probe for an ASR resistance allele corresponding to SEQ ID NO: 5.

SEQ ID NO: 50 is a hybridization probe for an ASR susceptibility allele corresponding to SEQ ID NO: 5.

SEQ ID NO: 51 is a hybridization probe for an ASR resistance allele corresponding to SEQ ID NO: 6.

SEQ ID NO: 52 is a hybridization probe for an ASR susceptibility allele corresponding to SEQ ID NO: 6.

SEQ ID NO: 53 is a hybridization probe for an ASR resistance allele corresponding to SEQ ID NO: 7.

SEQ ID NO: 54 is a hybridization probe for an ASR susceptibility allele corresponding to SEQ ID NO: 7.

SEQ ID NO: 55 is a hybridization probe for an ASR resistance allele corresponding to SEQ ID NO: 8.

SEQ ID NO: 56 is a hybridization probe for an ASR susceptibility allele corresponding to SEQ ID NO: 8.

SEQ ID NO: 57 is a single base extension (SBE) probe for an ASR resistance allele corresponding to SEQ ID NO: 1.

SEQ ID NO: 58 is a single base extension (SBE) probe for an ASR resistance allele corresponding to SEQ ID NO: 1.

SEQ ID NO: 59 is a single base extension (SBE) probe for an ASR resistance allele corresponding to SEQ ID NO: 2.

SEQ ID NO: 60 is a single base extension (SBE) probe for an ASR resistance allele corresponding to SEQ ID NO: 2.

SEQ ID NO: 61 is a single base extension (SBE) probe for an ASR resistance allele corresponding to SEQ ID NO: 3.

SEQ ID NO: 62 is a single base extension (SBE) probe for an ASR resistance allele corresponding to SEQ ID NO: 3.

SEQ ID NO: 63 is a single base extension (SBE) probe for an ASR resistance allele corresponding to SEQ ID NO: 4.

SEQ ID NO: 64 is a single base extension (SBE) probe for an ASR resistance allele corresponding to SEQ ID NO: 4.

SEQ ID NO: 65 is a single base extension (SBE) probe for an ASR resistance allele corresponding to SEQ ID NO: 5.

SEQ ID NO: 66 is a single base extension (SBE) probe for an ASR resistance allele corresponding to SEQ ID NO: 5.

SEQ ID NO: 67 is a single base extension (SBE) probe for an ASR resistance allele corresponding to SEQ ID NO: 6.

SEQ ID NO: 68 is a single base extension (SBE) probe for an ASR resistance allele corresponding to SEQ ID NO: 6.

SEQ ID NO: 69 is a single base extension (SBE) probe for an ASR resistance allele corresponding to SEQ ID NO: 7.

SEQ ID NO: 70 is a single base extension (SBE) probe for an ASR resistance allele corresponding to SEQ ID NO: 7.

SEQ ID NO: 71 is a single base extension (SBE) probe for an ASR resistance allele corresponding to SEQ ID NO: 8.

SEQ ID NO: 72 is a single base extension (SBE) probe for an ASR resistance allele corresponding to SEQ ID NO: 8.

SEQ ID NO: 73 is ASR resistance allele 1 corresponding to SEQ ID NO: 1.

SEQ ID NO: 74 is ASR resistance allele 2 corresponding to SEQ ID NO: 2.

SEQ ID NO: 75 is ASR resistance allele 3 corresponding to SEQ ID NO: 3.

SEQ ID NO: 76 is ASR resistance allele 4 corresponding to SEQ ID NO: 4.

SEQ ID NO: 77 is ASR resistance allele 5 corresponding to SEQ ID NO: 5.

SEQ ID NO: 78 is ASR resistance allele 6 corresponding to SEQ ID NO: 6.

SEQ ID NO: is an ASR resistance allele 7 corresponding to SEQ ID NO: 7.

SEQ ID NO: 80 is ASR resistance allele 8 corresponding to SEQ ID NO: 8.

DETAILED DESCRIPTION OF THE INVENTION

Figure 1:
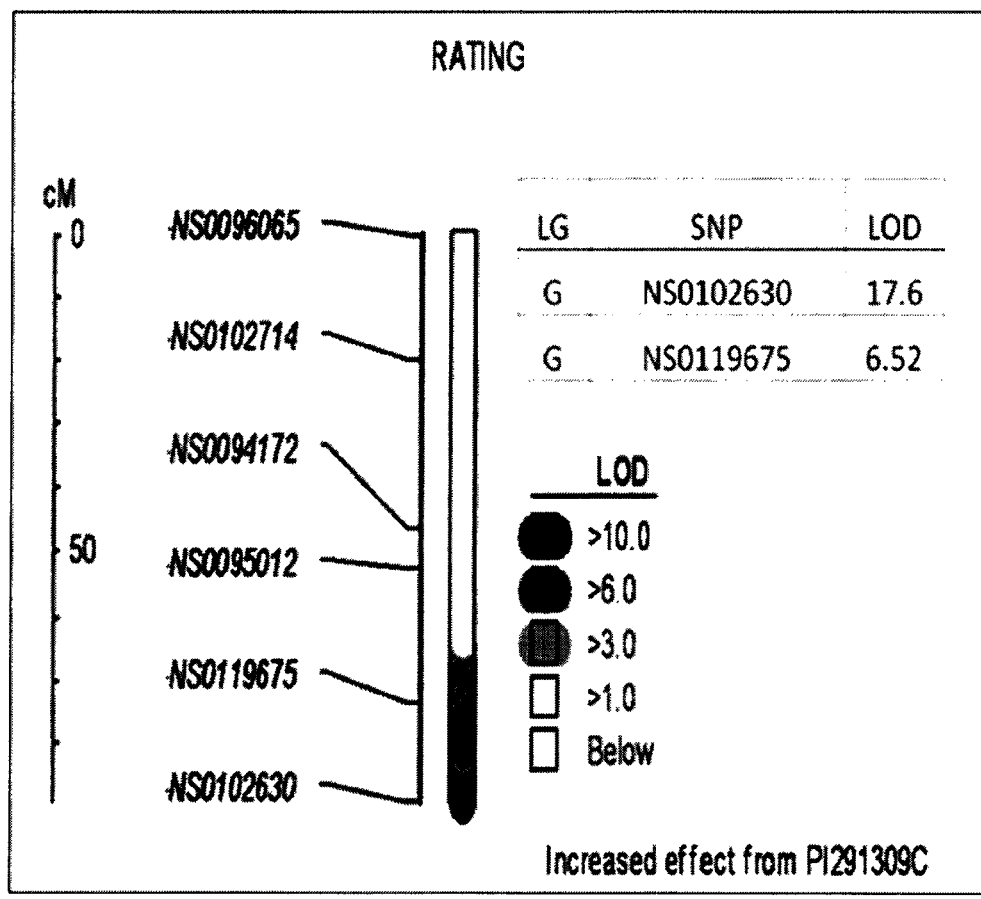
FIG. 1 depicts the positions of ASR locus 14 on linkage group G. To the right is the legend for the LOD plot for the population. The black bar indicates the confidence interval for the position of NS0102630 (LOD>10). The gray bar indicates the confidence interval for the position of NS0119675 (LOD>2).

The definitions and methods provided define the present invention and guide those of ordinary skill in the art in the practice of the present invention. Unless otherwise noted, terms are to be understood according to conventional usage by those of ordinary skill in the relevant art. Definitions of common terms in molecular biology may also be found in Alberts et al., Molecular Biology of The Cell, 5$^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed, Oxford University Press: New York, 2002; and Lewin, Genes IX, Oxford University Press: New York, 2007. The nomenclature for DNA bases as set forth at 37 CFR §1.822 is used.

An "allele" refers to an alternative sequence at a particular locus; the length of an allele can be as small as 1 nucleotide base, but is typically larger. Allelic sequence can be denoted as nucleic acid sequence or as amino acid sequence that is encoded by the nucleic acid sequence.

A "locus" is a position on a genomic sequence that is usually found by a point of reference; e.g., a short DNA sequence that is a gene, or part of a gene or intergenic region. The loci of this invention comprise one or more polymorphisms in a population; i.e., alternative alleles present in some individuals.

As used herein, "polymorphism" means the presence of one or more variations of a nucleic acid sequence at one or more loci in a population of one or more individuals. The variation may comprise but is not limited to one or more base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found, or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs) a restriction fragment length polymorphism, and a tag SNP. A genetic marker, a gene, a DNA-derived sequence, a haplotype, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may comprise polymorphisms.

As used herein, "marker" means a polymorphic nucleic acid sequence or nucleic acid feature. A marker may be represented by one or more particular variant sequences, or by a consensus sequence. In another sense, a "marker" is an isolated variant or consensus of such a sequence. In a broader aspect, a "marker" can be a detectable characteristic that can be used to discriminate between heritable differences between organisms. Examples of such characteristics may include genetic markers, protein composition, protein levels, oil composition, oil levels, carbohydrate composition, carbohydrate levels, fatty acid composition, fatty acid levels, amino acid composition, amino acid levels, biopolymers, pharmaceuticals, starch composition, starch levels, fermentable starch, fermentation yield, fermentation efficiency, energy yield, secondary compounds, metabolites, morphological characteristics, and agronomic characteristics.

As used herein, "marker assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "typing" refers to any method whereby the specific allelic form of a given soybean genomic polymorphism is determined. For example, a single nucleotide polymorphism (SNP) is typed by determining which nucleotide is present (i.e. an A, G, T, or C). Insertion/deletions (Indels) are determined by determining if the Indel is present. Indels can be typed by a variety of assays including, but not limited to, marker assays.

As used herein, the phrase "adjacent", when used to describe a nucleic acid molecule that hybridizes to DNA containing a polymorphism, refers to a nucleic acid that hybridizes to DNA sequences that directly or nearly abut the polymorphic nucleotide base position. For example, a nucleic acid molecule that can be used in a single base extension assay is "adjacent" to the polymorphism.

As used herein, "interrogation position" refers to a physical position on a solid support that can be queried to obtain genotyping data for one or more predetermined genomic polymorphisms.

As used herein, "consensus sequence" refers to a constructed DNA sequence which identifies SNP and Indel polymorphisms in alleles at a locus. Consensus sequence can be based on either strand of DNA at the locus and states the nucleotide base of either one of each SNP in the locus and the nucleotide bases of all Indels in the locus. Thus, although a consensus sequence may not be a copy of an actual DNA sequence, a consensus sequence is useful for precisely designing primers and probes for actual polymorphisms in the locus.

As used herein, the term "single nucleotide polymorphism," also referred to by the abbreviation "SNP," means a polymorphism at a single site wherein said polymorphism constitutes a single base pair change, an insertion of one or more base pairs, or a deletion of one or more base pairs.

As used herein, the term "haplotype" means a chromosomal region within a haplotype window defined by an allele of at least one polymorphic molecular marker. The unique marker fingerprint combinations in each haplotype window define individual haplotypes for that window. Further, changes in a haplotype, brought about by recombination for example, may result in the modification of a haplotype so that it comprises only a portion of the original (parental) haplotype operably linked to the trait, for example, via physical linkage to a gene, QTL, or transgene. Any such change in a haplotype would be included in our definition of what constitutes a haplotype so long as the functional integrity of that genomic region is unchanged or improved.

As used herein, the term "haplotype window" means a chromosomal region that is established by statistical analyses known to those of skill in the art and is in linkage disequilibrium. Thus, identity by state between two inbred individuals (or two gametes) at one or more molecular marker loci located within this region is taken as evidence of identity-by-descent of the entire region. Each haplotype window includes at least one polymorphic molecular marker. Haplotype windows can be mapped along each chromosome in the genome. Haplotype windows are not fixed per se and, given the ever-increasing density of molecular markers, this invention anticipates the number and size of haplotype windows to evolve, with the number of windows increasing and their respective sizes decreasing, thus resulting in an ever-increasing degree confidence in ascertaining identity by descent based on the identity by state at the marker loci.

As used herein, "genotype" means the genetic component of the phenotype and it can be indirectly characterized using markers or directly characterized by nucleic acid sequencing. Suitable markers include a phenotypic character, a metabolic profile, a genetic marker, or some other type of marker. A genotype may constitute an allele for at least one genetic marker locus or a haplotype for at least one haplotype window. In some embodiments, a genotype may represent a single locus and in others it may represent a genome-wide set of loci. In another embodiment, the genotype can reflect the sequence of a portion of a chromosome, an entire chromosome, a portion of the genome, and the entire genome.

As used herein, "phenotype" means the detectable characteristics of a cell or organism which can be influenced by gene expression.

As used herein, "linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ are attributed to linkage.

As used herein, "linkage disequilibrium" is defined in the context of the relative frequency of gamete types in a population of many individuals in a single generation. If the frequency of allele A is p, a is p', B is q and b is q', then the expected frequency (with no linkage disequilibrium) of genotype AB is pq, Ab is pq', aB is p'q and ab is p'q'. Any deviation from the expected frequency is called linkage disequilibrium. Two loci are said to be "genetically linked" when they are in linkage disequilibrium.

As used herein, "quantitative trait locus (QTL)" means a locus that controls to some degree numerically representable traits that are usually continuously distributed.

As used herein, "immunity" means an ASR disease phenotype exhibiting no lesions visible to the unaided eye, or red-brown lesions not associated with pustules or viable spores and having a length averaging no larger than about one fourth the average length of lesions of the susceptible phenotype assayed under comparable conditions, and covering no more than about one twentieth of the leaf surface area. The numerical score for complete immunity is 1; for immunity with small but visible lesions or discolorations, the numerical score is 1.5.

As used herein, "resistance" means an ASR disease phenotype exhibiting either immunity or red-brown lesions that may or may not be associated with pustules or viable spores, or may be delayed in sporulation, having a length averaging about one fourth to the same length as the average length of lesions of the susceptible phenotype assayed under comparable conditions, the degree of resistance varying inversely with the percentage of the leaf surface area coverage. The numerical score for resistance is 2 if less than about 50% of the leaf is covered with lesions, and 3 if greater than about 50% of the leaf is covered. A leaf having about 50% of its area covered with red-brown lesions has a numerical score of 2.5.

As used herein, "susceptibility" means an ASR disease phenotype exhibiting tan lesions associated with pustules containing viable spores and having a length averaging about 2 mm to 5 mm under the standard assay conditions used (U.S. application Ser. No. 11/805,667), the degree of susceptibility varying directly with the percentage of the leaf surface area coverage. The numerical score for susceptibility is 4 if less than about 50% of the leaf is covered with lesions, and 5 if greater than about 50% of the leaf is covered. A leaf having about 50% of its area covered with tan lesions has a numerical score of 4.5.

A response score can also reflect an average score for multiple leaves or tests, such that scores may have numerical values between whole numbers, typically expressed as decimals.

As used herein, "resistance allele" means the isolated nucleic acid sequence that includes the polymorphic allele associated with resistance to ASR.

As used herein, the term "soybean" means *Glycine max* and includes all plant varieties that can be bred with soybean, including wild soybean species.

As used herein, the term "comprising" means "including but not limited to".

As used herein, the term "elite line" means any line that has resulted from breeding and selection for superior agronomic performance. An elite plant is any plant from an elite line.

The present invention provides an ASR resistance QTL that maps to a region on Linkage Group G close to Rpp1; however, the present invention, designated ASR resistance locus 14, is distinct from Rpp1 in having a red-brown phenotype of lesions covering about less than 25% of the surface area of the leaf, whereas Rpp1 typically confers immunity to ASR. The present invention also provides methods and compositions for selecting and introgressing a QTL capable of conferring resistance to ASR from a source derived from PI291309C. A QTL that is located at ASR resistance locus 14 is provided.

The present invention provides an ASR resistance QTL that maps to a region on Linkage Group C2; the present invention, designated ASR resistance locus 15, has a red-brown phenotype of lesions covering about less than 25% of the surface area of the leaf. The present invention further provides an ASR resistance QTL that maps to a region on Linkage Group D2; the present invention, designated ASR resistance locus 16, has a red-brown phenotype of lesions covering about less than 25% of the surface area of the leaf. The present invention also provides methods and compositions for selecting and introgressing QTLs capable of conferring resistance to ASR from a source derived from PI507009. QTLs that are located at ASR resistance loci 15 and 16 are provided.

In the present invention, an ASR resistance locus, ASR resistance locus 14, is located on Linkage Group G. SNP markers used to monitor the introgression of ASR resistance locus 14 include those selected from the group consisting of NS0119675, NS0095012 and NS0102630. Illustrative ASR resistance locus 14 SNP marker DNA sequence SEQ ID NO: 1 can be amplified using the primers indicated as SEQ ID NO: 9 and 10 and detected with probes indicated as SEQ ID NO: 25 and 26; SEQ ID NO: 2 can be amplified using the primers indicated as SEQ ID NO: 11 and 12 and detected with probes indicated as SEQ ID NO: 27 and 28; SEQ ID NO: 3 can be amplified using the primers indicated as SEQ ID NO: 13 and 14 and detected with probes indicated as SEQ ID NO: 29 and 30.

Similarly, the present invention, an ASR resistance locus, ASR resistance locus 15, is located on Linkage Group C2. SNP markers used to monitor the introgression of ASR resistance locus 15 include those selected from the group consisting of NS0093385, NS0118716 and NS0127833. Illustrative ASR resistance locus 15 SNP marker DNA sequence SEQ ID NO: 4 can be amplified using the primers indicated as SEQ ID NO: 15 and 16 and detected with probes indicated as SEQ ID NO: 31 and 32; SEQ ID NO: 5 can be amplified using the primers indicated as SEQ ID NO: 17 and 18 and detected with probes indicated as SEQ ID NO: 33 and 34; SEQ ID NO: 6 can be amplified using the primers indicated as SEQ ID NO: 19 and 20 and detected with probes indicated as SEQ ID NO: 35 and 36.

In the present invention, an ASR resistance locus, ASR resistance locus 16, is located on Linkage Group D2. SNP markers used to monitor the introgression of ASR resistance locus 16 include those selected from the group consisting of NS0113966 and NS0118536. Illustrative ASR resistance locus 16 SNP marker DNA sequence SEQ ID NO: 7 can be amplified using the primers indicated as SEQ ID NO: 21 and 22 and detected with probes indicated as SEQ ID NO: 37 and 38; SEQ ID NO: 8 can be amplified using the primers indicated as SEQ ID NO: 23 and 24 and detected with probes indicated as SEQ ID NO: 39 and 40.

The present invention also provides a soybean plant comprising a nucleic acid molecule selected from the group consisting of SEQ ID NO: 73 through 80 and complements thereof. The present invention also provides a soybean plant comprising a nucleic acid molecule selected from the group consisting of SEQ ID NO: 1 though 8, fragments thereof, and complements of both. The present invention also provides a soybean plant comprising a nucleic acid molecule selected from the group consisting of SEQ ID NO: 9 through 72, fragments thereof, and complements of both.

In one aspect, the soybean plant comprises the 3 nucleic acid molecules SEQ ID NO: 73 through 75 and complements thereof. In another aspect, the soybean plant comprises the 3 nucleic acid molecules SEQ ID NO: 1 through 3, fragments thereof, and complements of both. In a further aspect, the soybean plant comprises 2, 3, 4, 5, 6, 7, 8, 9, 10, 11 or 12 nucleic acid molecules selected from the group consisting of SEQ ID NO: 9 through 14 and 25 through 30, fragments thereof, and complements thereof.

In another aspect, the soybean plant comprises the 3 nucleic acid molecules SEQ ID NO: 76 through 78 and complements thereof. In another aspect, the soybean plant comprises the 3 nucleic acid molecules SEQ ID NO: 4 through 6, fragments thereof, and complements of both. In a further aspect, the soybean plant comprises 2, 3, 4, 5, 6, 7, 8, 9, 10, 11 or 12 nucleic acid molecules selected from the group consisting of SEQ ID NO: 15 through 20 and 31 through 36, fragments thereof, and complements thereof.

In another aspect, the soybean plant comprises the 2 nucleic acid molecules SEQ ID NO: 79 and 80 and complements thereof. In another aspect, the soybean plant comprises the 2 nucleic acid molecules SEQ ID NO: 7 and 8, fragments thereof, and complements of both. In a further aspect, the soybean plant comprises 2, 3, 4, 5, 6, 7 or 8 nucleic acid molecules selected from the group consisting of SEQ ID NO: 21 through 24 and 37 through 40, fragments thereof, and complements thereof.

In another aspect, the soybean plant comprises the 5 nucleic acid molecules SEQ ID NO: 76 through 80 and complements thereof. In another aspect, the soybean plant comprises the 5 nucleic acid molecules SEQ ID NO: 4 through 8, fragments thereof, and complements of both. In a further aspect, the soybean plant comprises 2, 3, 4, 5, 6, 7, 8, 9, 10, 11, 12, 13, 14, 15, 16, 17, 18, 19 or 20 nucleic acid molecules selected from the group consisting of SEQ ID NO: 15 through 24 and 31 through 40, fragments thereof, and complements thereof.

In another aspect, the soybean plant comprises the 6 nucleic acid molecules SEQ ID NO: 73 through 78 and complements thereof. In another aspect, the soybean plant comprises the 6 nucleic acid molecules SEQ ID NO: 1 through 6, fragments thereof, and complements of both. In a further aspect, the soybean plant comprises 2, 3, 4, 5, 6, 7, 8, 9, 10, 11, 12, 13, 14, 15, 16, 17, 18, 19, 20, 21, 22, 23 or 24 nucleic acid molecules selected from the group consisting of SEQ ID NO: 9 through 20 and 25 through 36, fragments thereof, and complements thereof.

In another aspect, the soybean plant comprises the 5 nucleic acid molecules SEQ ID NO: 73, 74, 75, 79 and 80 and complements thereof. In another aspect, the soybean plant comprises the 5 nucleic acid molecules SEQ ID NO: 1, 2, 3, 7 and 8, fragments thereof, and complements of both. In a further aspect, the soybean plant comprises 2, 3, 4, 5, 6, 7, 8, 9, 10, 11, 12, 13, 14, 15, 16, 17, 18, 19 or 20 nucleic acid molecules selected from the group consisting of SEQ ID NO: 9 through 14, 21 through 30 and 37 through 40, fragments thereof, and complements thereof.

The present invention also provides a soybean plant comprising an ASR resistance locus 14. Said allele may be homozygous or heterozygous. The present invention also provides a soybean plant comprising an ASR resistance locus 15. Said allele may be homozygous or heterozygous. The present invention also provides a soybean plant comprising an ASR resistance locus 16. Said allele may be homozygous or heterozygous. The present invention also provides a soybean plant comprising two or more ASR resistance loci from the group consisting of ASR resistance loci 14, 15 and 16. Said alleles may be homozygous or heterozygous.

In one embodiment, any single ASR resistance locus 14, 15 or 16, or any combination of these ASR resistance loci, can be combined with one or more other ASR resistance loci in a breeding program to produce a soybean plant with at least two ASR resistance loci, as described in U.S. patent application Ser. No. 11/805,667.

As used herein, ASR refers to any ASR variant or isolate. A soybean plant of the present invention can be resistant to one or more fungi capable of causing or inducing ASR. In one aspect, the present invention provides plants resistant or tolerant to ASR as well as methods and compositions for screening soybean plants for resistance or susceptibility to ASR, caused by the genus *Phakopsora*. In a preferred aspect, the present invention provides methods and compositions for screening soybean plants for resistance or susceptibility to *Phakopsora pachyrhizi*. In another aspect, the present invention provides plants resistant to and methods and compositions for screening soybean plants for resistance or susceptibility to *Phakopsora pachyrhizi* strain "MBH1," originally isolated in southeastern Missouri.

The present invention further provides that the selected plant is from the group consisting of members of the genus *Glycine*, more specifically from the group consisting of *Glycine arenaria*, *Glycine argyrea*, *Glycine canescens*, *Glycine clandestine*, *Glycine curvata*, *Glycine cyrtoloba*, *Glycine falcate*, *Glycine latifolia*, *Glycine latrobeana*, *Glycine max*, *Glycine microphylla*, *Glycine pescadrensis*, *Glycine pindanica*, *Glycine rubiginosa*, *Glycine soja*, *Glycine* sp., *Glycine stenophita*, *Glycine tabacina* and *Glycine tomentella*.

Plants of the present invention include a soybean plant that has a resistance level of from 1 to 5, 1 being completely immune, 2 being resistant to substantially resistant, 3 being mid-resistant to partially resistant, 4 being mid-susceptible, and 5 being susceptible, when assayed for resistance or susceptibility to ASR by any method and rated as such according to the numerical scale described herein.

In a preferred aspect, the present invention provides a soybean plant to be assayed for resistance or susceptibility to ASR by any method to determine whether a soybean plant has a resistance level of from 1 to 5, 1 being completely immune, 2 being resistant to substantially resistant, 3 being mid-resistant to partially resistant, 4 being mid-susceptible, and 5 being susceptible, according to the numerical scale described herein.

In light of the generally acknowledged impact of ASR on yield, another aspect of the present invention provides plants and derivatives thereof of soybean with one or more ASR resistance loci that exhibit increased grain yield in the presence of ASR compared to soybean plants lacking ASR resistance loci. In certain embodiments, the increase in grain of plants of the invention in the presence of ASR may be at least 0.5, 1, 1.5, 2.0, 2.5, or 3 bushels/acre as compared to soybean plants lacking ASR resistance loci.

A disease resistance QTL of the present invention may be introduced into an elite soybean inbred line. An "elite line" is any line that has resulted from breeding and selection for superior agronomic performance. Non-limiting examples of elite soybean varieties that are commercially available to farmers or soybean breeders include AG00802, A0868, AG0902, A1923, AG2403, A2824, A3704, A4324, A5404, AG5903 and AG6202 (Asgrow Seeds, Des Moines, Iowa, USA); BPR0144RR, BPR 4077NRR and BPR 4390NRR (Bio Plant Research, Camp Point, Ill., USA); DKB17-51 and DKB37-51 (DeKalb Genetics, DeKalb, Ill., USA); and DP 4546 RR, and DP 7870 RR (Delta & Pine Land Company, Lubbock, Tex., USA); JG 03R501, JG 32R606C ADD and JG 55R503C (JGL Inc., Greencastle, Ind., USA); NKS13-K2 (NK Division of Syngenta Seeds, Golden Valley, Minn., USA); 90M01, 91M30, 92M33, 93M11, 94M30, 95M30 and 97B52 (Pioneer Hi-Bred International, Johnston, Iowa, USA); SG4771NRR and SG5161NRR/STS (Soygenetics, LLC, Lafayette, Ind., USA); S00-K5, S11-L2, S28-Y2, S43-B1, S53-A1, S76-L9 and S78-G6 (Syngenta Seeds, Henderson, Ky., USA). An elite plant is a representative plant from an elite variety.

An ASR resistance locus of the present invention may also be introduced into an elite soybean plant comprising one or more transgenes conferring herbicide tolerance, increased yield, insect control, fungal disease resistance, virus resistance, nematode resistance, bacterial disease resistance, *mycoplasma* disease resistance, modified oils production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid seed production, reduced allergenicity, biopolymers, and biofuels among others. In one aspect, the herbicide tolerance is selected from the group consisting of glyphosate, dicamba, glufosinate, sulfonylurea, bromoxynil and norflurazon herbicides. These traits can be provided by methods of plant biotechnology as transgenes in soybean.

A disease resistance QTL allele or alleles can be introduced from any plant that contains that allele (donor) to any recipient soybean plant. In one aspect, the recipient soybean plant can contain additional ASR resistance loci. In another aspect, the recipient soybean plant can contain a transgene. In another aspect, while maintaining the introduced QTL, the genetic contribution of the plant providing the disease resistance QTL can be reduced by back-crossing or other suitable approaches. In one aspect, the nuclear genetic material derived from the donor material in the soybean plant can be less than or about 50%, less than or about 25%, less than or about 13%, less than or about 5%, 3%, 2% or 1%, but that genetic material contains the ASR resistance locus of interest.

Plants containing one or more ASR resistance loci described can be donor plants. Soybean plants containing resistance loci can be, for example, screened for by using a nucleic acid molecule capable of detecting a marker polymorphism associated with resistance. In one aspect, a donor plant is selected from the group consisting of PI291309C and PI507009. In another aspect, a donor plant is derived from PI291309C or from PI507009. In another aspect, a donor plant is derived from both PI291309C and PI507009 by a sexual cross, transformation or other gene combination method that brings at least one ASR resistance gene from each of these lines together in the donor plant. A donor plant can be a susceptible line. In one aspect, a donor plant can also be a recipient soybean plant.

It is further understood that a soybean plant of the present invention may exhibit the characteristics of any relative maturity group. In an aspect, the maturity group is selected from the group consisting of 000, 00, 0, 1, 2, 3, 4, 5, 6, 7, 8, 9, and 10.

An allele of a QTL can, of course, comprise multiple genes or other genetic factors even within a contiguous genomic region or linkage group, such as a haplotype. As used herein, an allele of a disease resistance locus can therefore encompass more than one gene or other genetic factor where each individual gene or genetic component is also capable of exhibiting allelic variation and where each gene or genetic factor is also capable of eliciting a phenotypic effect on the quantitative trait in question. In an aspect of the present invention the allele of a QTL comprises one or more genes or other genetic factors that are also capable of exhibiting allelic variation. The use of the term "an allele of a QTL" is thus not intended to exclude a QTL that comprises more than one gene or other genetic factor. Specifically, an "allele of a QTL" in the present invention can denote a haplotype within a haplotype window wherein a phenotype can be disease resistance. A haplotype window is a contiguous genomic region that can be defined, and tracked, with a set of one or more polymorphic markers wherein the polymorphisms indicate identity by descent. A haplotype within that window can be defined by the unique fingerprint of alleles at each marker. As used herein, an allele is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus. Plants of the present invention may be homozygous or heterozygous at any particular ASR locus or for a particular polymorphic marker.

The present invention also provides for parts of the plants of the present invention. Plant parts, without limitation, include seed, endosperm, ovule, pollen, stems, cuttings, cells, protoplasts, and tissue cultures. In a particularly preferred aspect of the present invention, the plant part is a seed.

The present invention also provides a container of soybean seed in which greater than 50%, 60%, 70%, 80%, 90%, 95%, or 99% of the seeds comprise at least one locus from the group consisting of ASR resistance loci 14, 15 and 16.

The container of soybean seeds can contain any number, weight, or volume of seeds. For example, a container can contain at least, or greater than, about 10, 25, 50, 100, 200, 300, 400, 500, 600, 700, 80, 90, 1000, 1500, 2000, 2500, 3000, 3500, 4000 or more seeds. In another aspect, a container can contain about, or greater than about, 1 gram, 5 grams, 10 grams, 15 grams, 20 grams, 25 grams, 50 grams, 100 grams, 250 grams, 500 grams, or 1000 grams of seeds. Alternatively, the container can contain at least, or greater than, about 0 ounces, 1 ounce, 5 ounces, 10 ounces, 1 pound, 2 pounds, 3 pounds, 4 pounds, 5 pounds, 10 pounds, 15 pounds, 20 pounds, 25 pounds, or 50 pounds or more seeds.

Containers of soybean seeds can be any container available in the art. For example, a container can be a box, a bag, a can, a packet, a pouch, a tape roll, a pail, or a tube.

In another aspect, the seeds contained in the containers of soybean seeds can be treated or untreated soybean seeds. In one aspect, the seeds can be treated to improve germination, for example, by priming the seeds, or by disinfection to protect against seed-born pathogens. In another aspect, seeds can be coated with any available coating to improve, for example, plantability, seed emergence, and protection against seed-born pathogens. Seed coating can be any form of seed coating including, but not limited to, pelleting, film coating, and encrustments.

Plants or parts thereof of the present invention may be grown in culture and regenerated. Methods for the regeneration of *Glycine max* plants from various tissue types and methods for the tissue culture of *Glycine max* are known in the art (See, for example, Widholm et al., *In Vitro Selection and Culture-induced Variation in Soybean*, In Soybean: Genetics, Molecular Biology and Biotechnology, Eds. Verma and Shoemaker, CAB International, Wallingford, Oxon, England (1996). Regeneration techniques for plants such as *Glycine max* can use as the starting material a variety of tissue or cell types. With *Glycine max* in particular, regeneration processes have been developed that begin with certain differentiated tissue types such as meristems, Cartha et al., *Can. J. Bot.* 59:1671-1679 (1981), hypocotyl sections, Cameya et al., *Plant Science Letters* 21: 289-294 (1981), and stem node segments, Saka et al., *Plant Science Letters*, 19: 193-201 (1980); Cheng et al., *Plant Science Letters*, 19: 91-99 (1980). Regeneration of whole sexually mature *Glycine max* plants from somatic embryos generated from explants of immature *Glycine max* embryos has been reported (Ranch et al., *In Vitro Cellular & Developmental Biology* 21: 653-658 (1985). Regeneration of mature *Glycine max* plants from tissue culture by organogenesis and embryogenesis has also been reported (Barwale et al., *Planta* 167: 473-481 (1986); Wright et al., *Plant Cell Reports* 5: 150-154 (1986).

The present invention also provides a disease resistant soybean plant selected for by screening for disease resistance or susceptibility in the soybean plant, the selection comprising interrogating genomic nucleic acids for the presence of a marker molecule that is genetically linked to an allele of a QTL associated with disease resistance in the soybean plant, where the allele of a QTL is also located on a linkage group associated with resistance to ASR.

A method of introgressing an allele into a soybean plant comprising (A) crossing at least one first soybean plant comprising a nucleic acid molecule selected from the group consisting of SEQ ID NO: 73 through 80 with at least one second soybean plant in order to form a population, (B) screening the population with one or more nucleic acid markers to determine if one or more soybean plants from the population contains the nucleic acid molecule, and (C) selecting from the population one or more soybean plants comprising a nucleic acid molecule selected from the group consisting of SEQ ID NO: 73 through 80.

The present invention also includes a method of introgressing an allele into a soybean plant comprising: (A) crossing at least one ASR resistant soybean plant with at least one ASR sensitive soybean plant in order to form a population; (B) screening the population with one or more nucleic acid markers to determine if one or more soybean plants from the population contains at least one ASR resistance allele, wherein each ASR resistance allele is at a resistance locus selected from the group consisting of ASR resistance loci 14, 15 and 16.

The present invention includes isolated nucleic acid molecules. Such molecules include those nucleic acid molecules capable of detecting a polymorphism genetically or physically linked to an ASR locus. Such molecules can be referred to as markers. Additional markers can be obtained that are linked to a locus selected from the group consisting of ASR resistance loci 14, 15 and 16 by available techniques. In one aspect, the nucleic acid molecule is capable of detecting the presence or absence of a marker located less than 30, 20, 10, 5, 2, or 1 centimorgans from a locus selected from the group consisting of ASR resistance loci 14, 15 and 16. Exemplary nucleic acid molecules with corresponding map positions are provided in US Patent Application Nos. 2005/0204780, 2005/0216545, and Ser. No. 60/932,533, which can be used to facilitate selection and introgression of the loci of the present invention. In another aspect, a marker exhibits a LOD score of 2 or greater, 3 or greater, or 4 or greater with ASR resistance, measuring using a method known in the art such as Qgene Version 2.23 (1996) and default parameters. In another aspect, the nucleic acid molecule is capable of detecting a marker in a locus selected from the group consisting of the ASR resistance loci 14, 15 and 16. In a further aspect, a nucleic acid molecule is selected from the group consisting of SEQ ID NO: 1 through SEQ ID NO: 80, fragments thereof, complements thereof, and nucleic acid molecules capable of specifically hybridizing to one or more of these nucleic acid molecules.

In a preferred aspect, a nucleic acid molecule of the present invention includes those that will specifically hybridize to one or more of the nucleic acid molecules set forth in SEQ ID NO::1 through SEQ ID NO: 80 or complements thereof or fragments of either under moderately stringent conditions, for example at about 2.0×SSC and about 65° C. In a particularly preferred aspect, a nucleic acid of the present invention will specifically hybridize to one or more of the nucleic acid molecules set forth in SEQ ID NO: 1 through SEQ ID NO: 80 or complements or fragments of either under high stringency conditions. In one aspect of the present invention, a preferred marker nucleic acid molecule of the present invention has the nucleic acid sequence set forth in SEQ ID NO: 1 through SEQ ID NO: 80 or complements thereof or fragments of either. In another aspect of the present invention, a preferred marker nucleic acid molecule of the present invention shares between 80% and 100% or 90% and 100% sequence identity with the nucleic acid sequences set forth in SEQ ID NO: 1 through SEQ ID NO: 80 or complements thereof or fragments of either. In a further aspect of the present invention, a preferred marker nucleic acid molecule of the present invention shares between 95% and 100% sequence identity with the sequences set forth in SEQ ID NO: 1 through SEQ ID NO: 80 or complements thereof or fragments of either. In a more preferred aspect of the present invention, a preferred marker nucleic acid molecule of the present invention shares between 98% and 100% sequence identity with the nucleic acid sequence set forth in SEQ ID NO: 1 through SEQ ID NO: 80 or complement thereof or fragments of either. In a more preferred aspect of the present invention, a preferred marker nucleic acid molecule of the present invention shares between 99% and 100% sequence identity with the nucleic acid sequence set forth in SEQ ID NO: 1 through SEQ ID NO: 80 or complement thereof or fragments of either. In a more preferred aspect of the present invention, a preferred marker nucleic acid molecule of the present invention shares 100% sequence identity with the nucleic acid sequence set forth in SEQ ID NO: 1 through SEQ ID NO: 80 or complement thereof or fragments of either.

Nucleic acid molecules or fragments thereof are capable of specifically hybridizing to other nucleic acid molecules under certain circumstances. As used herein, two nucleic acid molecules are capable of specifically hybridizing to one another if the two molecules are capable of forming an anti-parallel, double-stranded nucleic acid structure. A nucleic acid molecule is the "complement" of another nucleic acid molecule if they exhibit complete complementarity. As used herein, molecules are exhibit "complete complementarity" when every nucleotide of one of the molecules is complementary to a nucleotide of the other. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Conventional stringency conditions are described by Sambrook et al., In: *Molecular Cloning, A Laboratory Manual, 2nd Edition*, Cold Spring Harbor Press, Cold Spring Harbor, N.Y. (1989), and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The nucleic-acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52, 9.56-9.58; Kanehisa 1984 Nucl. Acids Res. 12:203-213; and Wetmur et al. 1968 J. Mol. Biol. 31:349-370. Appropriate stringency conditions that promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

For example, hybridization using DNA or RNA probes or primers can be performed at 65° C. in 6×SSC, 0.5% SDS, 5× Denhardt's, 100 µg/mL nonspecific DNA (e.g., sonicated salmon sperm DNA) with washing at 0.5× SSC, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA, RNA, or cDNA fragments.

A fragment of a nucleic acid molecule can be any sized fragment and illustrative fragments include fragments of nucleic acid sequences set forth in SEQ ID NO: 1 through SEQ ID NO: 80 and complements thereof. In one aspect, a fragment can be between 15 and 25, 15 and 30, 15 and 40, 15 and 50, 15 and 100, 20 and 25, 20 and 30, 20 and 40, 20 and 50, 20 and 100, 25 and 30, 25 and 40, 25 and 50, 25 and 100, 30 and 40, 30 and 50, and 30 and 100 nucleotides. In another aspect, the fragment can be greater than 10, 15, 20, 25, 30, 35, 40, 50, 100, or 250 nucleotides.

Additional genetic markers can be used to select plants with an allele of a QTL associated with fungal disease resistance of soybeans of the present invention. Examples of public marker databases include, for example Soybase, an Agricultural Research Service, United States Department of Agriculture.

Genetic markers of the present invention include "dominant" or "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

In another embodiment, markers, such as single sequence repeat markers (SSR), AFLP markers, RFLP markers, RAPD markers, phenotypic markers, isozyme markers, single nucleotide polymorphisms (SNPs), insertions or deletions (Indels), single feature polymorphisms (SFPs, for example, as described in Borevitz et al. 2003 Gen. Res. 13:513-523), microarray transcription profiles, DNA-derived sequences, and RNA-derived sequences that are genetically linked to or correlated with alleles of a QTL of the present invention can be utilized.

In one embodiment, nucleic acid-based analyses for the presence or absence of the genetic polymorphism can be used for the selection of seeds in a breeding population. A wide variety of genetic markers for the analysis of genetic polymorphisms are available and known to those of skill in the art. The analysis may be used to select for genes, QTL, alleles, or genomic regions (haplotypes) that comprise or are linked to a genetic marker.

Herein, nucleic acid analysis methods are known in the art and include, but are not limited to, PCR-based detection methods (for example, TaqMan assays), microarray methods, and nucleic acid sequencing methods. In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201, 184; U.S. Pat. No. 4,683,202; U.S. Pat. No. 4,582,788; and U.S. Pat. No. 4,683,194), using primer pairs that are capable of hybridizing to the proximal sequences that define a polymorphism in its double-stranded form Polymorphisms in DNA sequences can be detected or typed by a variety of effective methods well known in the art including, but not limited to, those disclosed in U.S. Pat. Nos. 5,468,613 and 5,217,863; 5,210,015; 5,876,930; 6,030,787; 6,004,744; 6,013,431; 5,595,890; 5,762,876; 5,945,283; 5,468,613; 6,090,558; 5,800,944; and 5,616,464, all of which are incorporated herein by reference in their entireties. However, the compositions and methods of this invention can be used in conjunction with any polymorphism typing method to type polymorphisms in soybean genomic DNA samples. These soybean genomic DNA samples used include but are not limited to soybean genomic DNA isolated directly from a soybean plant, cloned soybean genomic DNA, or amplified soybean genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800, 944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616, 464 employing at least one pair of probes having sequences homologous to adjacent portions of the target nucleic acid sequence and having side chains which non-covalently bind to form a stem upon base pairing of said probes to said target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of soybean genomic DNA which flanks a region containing the polymorphism to be assayed. Following amplification of the region of the soybean genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In a preferred method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

For the purpose of QTL mapping, the markers included should be diagnostic of origin in order for inferences to be made about subsequent populations. SNP markers are ideal for mapping because the likelihood that a particular SNP allele is derived from independent origins in the extant populations of a particular species is very low. As such, SNP markers are useful for tracking and assisting introgression of QTLs, particularly in the case of haplotypes.

The genetic linkage of additional marker molecules can be established by a gene mapping model such as, without limitation, the flanking marker model reported by Lander et al. (Lander et al. 1989 Genetics, 121:185-199), and the interval mapping, based on maximum likelihood methods described therein, and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y.). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander et al. (1989), and further described by Arús and Moreno-González, *Plant Breeding*, Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak et al. 1995 Genetics, 139:1421-1428). Multiple regression methods or models can be also be used, in which the trait is regressed on a large number of markers (Jansen, *Biometrics in Plant Breed*, van Oijen, Jansen (eds.) Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen et al. (Jansen et al. 1994 Genetics, 136:1447-1455) and Zeng (Zeng 1994 Genetics 136:1457-1468). Generally, the use of cofactors reduces the bias and sampling error of the estimated QTL positions (Utz and Melchinger, *Biometrics in Plant Breeding*, van Oijen, Jansen (eds.) Proceedings of the Ninth Meeting of the Eucarpia Section Biometrics in Plant Breeding, The Netherlands, pp. 195-204 (1994), thereby improving the precision and efficiency of QTL mapping (Zeng 1994). These models can be extended to multi-environment experiments to analyze genotype-environment interactions (Jansen et al. 1995 Theor. Appl. Genet. 91:33-3).

Selection of appropriate mapping populations is important to map construction. The choice of an appropriate mapping population depends on the type of marker systems employed (Tanksley et al., *Molecular mapping in plant chromosomes. chromosome structure and function: Impact of new concepts* J. P. Gustafson and R. Appels (Eds.) Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted×adapted).

An $F_2$ population is the first generation of self pollinating (selfing). Usually a single $F_1$ plant is selfed to generate a population segregating for all the genes in Mendelian (1:2:1) fashion. Maximum genetic information is obtained from a completely classified $F_2$ population using a codominant marker system (Mather, Measurement of Linkage in Heredity: Methuen and Co., (1938)). In the case of dominant markers, progeny tests (e.g. $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations (e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually >$F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter et al. 1992 Proc. Natl. Acad. Sci. (USA) 89:1477-1481). However, as the distance between markers becomes larger (i.e., loci become more independent), the information in RIL populations decreases dramatically.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al. 1992). Information obtained from backcross populations using either codominant or dominant markers is less than that obtained from $F_2$ populations because one, rather than two, recombinant gametes are sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore et al. 1991 Proc. Natl. Acad. Sci. (U.S.A.) 88:9828-9832). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). A cultivar is a race or variety of a plant species that has been created or selected intentionally and maintained through cultivation.

As used herein, the term progeny refers to a genetic descendant. The present invention provides for progeny produced by sexual or vegetative reproduction, grown from seeds, regenerated from the above-described plant parts, or regenerated from tissue culture of a cultivar or a progeny plant.

Molecular breeding is often referred to as marker-assisted selection (MAS) and marker-assisted breeding (MAB), wherein MAS refers to making breeding decisions on the basis of molecular marker genotypes and MAB is a general term representing the use of molecular markers in plant breeding. In these types of molecular breeding programs, genetic marker alleles can be used to identify plants that contain the desired genotype at one marker locus, several loci, or a haplotype, and that would be expected to transfer the desired genotype, along with a desired phenotype to their progeny. Markers are highly useful in plant breeding because once established, they are not subject to environmental or epistatic interactions. Furthermore, certain types of markers are suited for high throughput detection, enabling rapid identification in a cost effective manner.

Selected, non-limiting approaches for breeding the plants of the present invention are set forth below. A breeding program can be enhanced using marker assisted selection (MAS) on the progeny of any cross. MAS is a selection process where a trait of interest is selected not based on the trait itself but on a marker linked to it. For example if MAS is being used to select individuals with a disease, the level of disease is not quantified but rather a marker allele which is linked with disease is used to determine disease presence. The assumption is that linked allele associates with the gene and/or quantitative trait locus (QTL) of interest. MAS can be useful for traits that are difficult to measure, expensive to phenotype, exhibit low heritability, and/or are expressed late in plant development. It is understood that nucleic acid markers of the present invention can be used in a MAS (breeding) program. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred aspect, a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes.

Breeding lines can be tested and compared to appropriate standards in environments representative of the commercial target area(s) for two or more generations. The best lines are candidates for new commercial cultivars; those still deficient in traits may be used as parents to produce new populations for further selection.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Backcross breeding has been used to transfer genes for a simply inherited, highly heritable trait into a desirable homozygous cultivar or inbred line, which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have most attributes of the recurrent parent (e.g., cultivar) and, in addition, the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several reference books (Allard, "Principles of Plant Breeding," John Wiley & Sons, NY, U. of CA, Davis, Calif., 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, In: *Soybeans: Improvement, Production and Uses,* 2nd Edition, *Monograph.,* 16:249, 1987; Fehr, "Principles of variety development," *Theory and Technique,* (Vol. 1) and *Crop Species Soybean* (Vol. 2), Iowa State Univ., Macmillan Pub. Co., NY, 360-376, 1987).

An alternative to traditional QTL mapping involves achieving higher resolution by mapping haplotypes, versus individual markers (Fan et al. 2006 Genetics 172:663-686). This approach tracks blocks of DNA known as haplotypes, as defined by polymorphic markers, which are assumed to be identical by descent in the mapping population. This assumption results in a larger effective sample size, offering greater resolution of QTL. Methods for determining the statistical significance of a correlation between a phenotype and a genotype, in this case a haplotype, may be determined by any statistical test known in the art and with any accepted threshold of statistical significance being required. The application of particular methods and thresholds of significance are well with in the skill of the ordinary practitioner of the art.

It is further understood, that the present invention provides bacterial, viral, microbial, insect, mammalian and plant cells comprising the nucleic acid molecules of the present invention.

As used herein, a "nucleic acid molecule," be it a naturally occurring molecule or otherwise may be "substantially purified," if desired, referring to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the present invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic, and thus involve the capacity of the agent to mediate a chemical reaction or response.

The agents of the present invention may also be recombinant. As used herein, the term recombinant means any agent (e.g. DNA, peptide etc.), that is, or results, however indirect, from human manipulation of a nucleic acid molecule.

The agents of the present invention may be labeled with reagents that facilitate detection of the agent (e.g. fluorescent labels (Prober et al. 1987 Science 238:336-340; Albarella et al., European Patent 144914), chemical labels (Sheldon et al., U.S. Pat. No. 4,582,789; Albarella et al., U.S. Pat. No. 4,563,417), modified bases (Miyoshi et al., European Patent 119448).

Having now generally described the invention, the same will be more readily understood through reference to the following examples which are provided by way of illustration, and are not intended to be limiting of the present invention, unless specified.

EXAMPLES

Example 1

Testing of Soybean Accessions for ASR Resistance Using the Detached Leaf Assay

Forty putative ASR resistant accessions were screened for ASR resistance. Leaf assays for resistance to ASR were performed on these 40 lines, and appropriate susceptible accessions as controls, as described in U.S. patent application Ser. No. 11/805,667. Plants were scored as having a degree of resistance indicated by a numerical rating from 1 to 5; 1—being immune, 2—demonstrating red/brown lesions over less than about 50% of the leaf area, 3—demonstrating red/brown lesions over greater than about 50% of the leaf area, 4—demonstrating tan lesions over less than about 50% of the leaf area and 5—demonstrating tan lesions over greater than about 50% of the leaf area, i.e. completely susceptible. An average rust severity score over multiple tests of 1.5 was obtained for accession PI291309C, a maturity-group-2 line, and for PI507009, a maturity-group-6 line, when infected with a North American isolate of *P. pachyrhizi* MBH1 from southeastern Missouri.

PI291309C and PI507009 were each crossed with soybean line MV0079 to generate F2 mapping populations, individuals of which were genotyped with 104 SNPs and tested for ASR resistance. SNPs were selected based on the fingerprint profile of the parents and genome coverage. The ASR resistance locus discovered in PI291309C, designated ASR resistance locus 14, was mapped to linkage group G of the public soybean genetic linkage map close to the Rpp1 gene (FIG. 1). The ASR resistance locus characterized in PI291309C is distinct on a haplotype basis from soybean lines containing the ASR resistance locus designated Rpp1, as well as differing in phenotypic response to southeastern Missouri *P. pachyrhizi* strain MBH1. Three SNP markers, NS0095012 (P<0.0050) and NS0102630 and NS0119675 (P<0.0010 for each) were found to be in high linkage disequilibria with the ASR resistance locus 14 disease phenotypic response, and therefore associated with ASR resistance locus 14. All three SNP markers were identified as being useful in monitoring the positive introgression of ASR resistance locus 14. SNP marker NS0095012 corresponds to SEQ ID NO: 1; NS0119675 corresponds to SEQ ID NO: 2; and NS0102630 corresponds to SEQ ID NO: 3.

Figure 2:
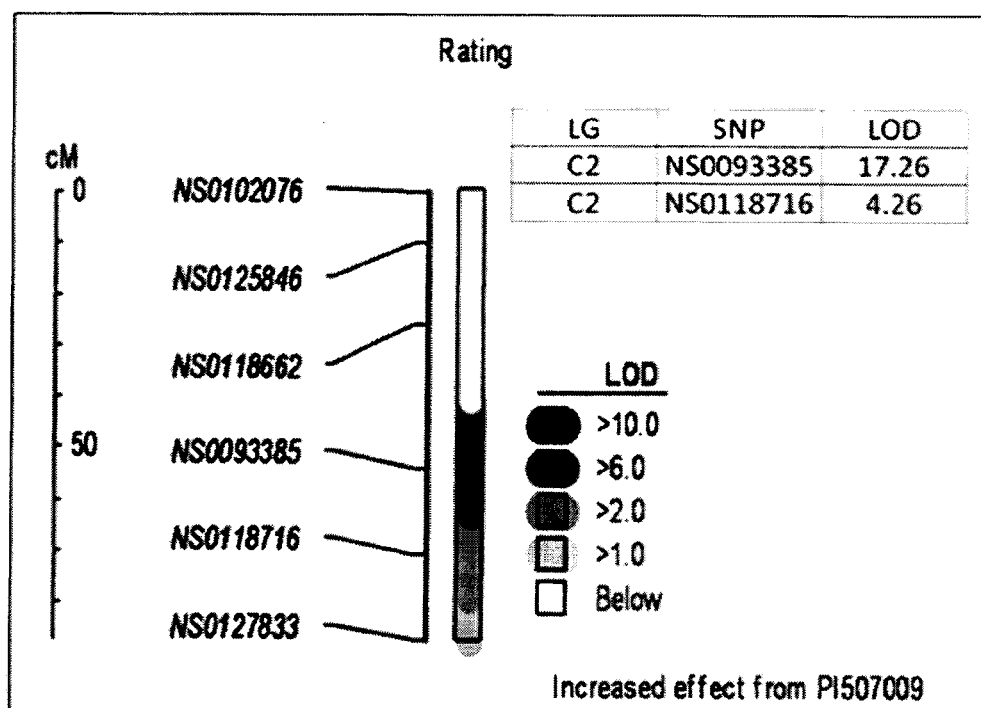
FIG. 2 depicts the positions of ASR locus 15 on linkage group C2. To the right is the legend for the LOD plot for the population. The black bar indicates the confidence interval for the position of NS0093385 (LOD>10). The dark gray bar indicates the confidence interval for the position of NS0118716 (LOD>2).

The ASR resistance locus 15 was discovered in PI507009 and mapped to linkage group C2 of the public soybean genetic linkage map (FIG. 2). Three SNP markers, NS0127833 (R Sq>0.050) and NS0118716 and NS0093385 (R Sq>0.200 for each) were found to be in high linkage disequilibria with the ASR resistance locus 15 disease phenotypic response, and therefore associated with ASR resistance locus 15. All three SNP markers were identified as being useful in monitoring the positive introgression of ASR resistance locus 15. SNP marker NS0093385 corresponds to SEQ ID NO: 4; NS0118716 corresponds to SEQ ID NO: 5; and NS0127833 corresponds to SEQ ID NO: 6.

Figure 3:
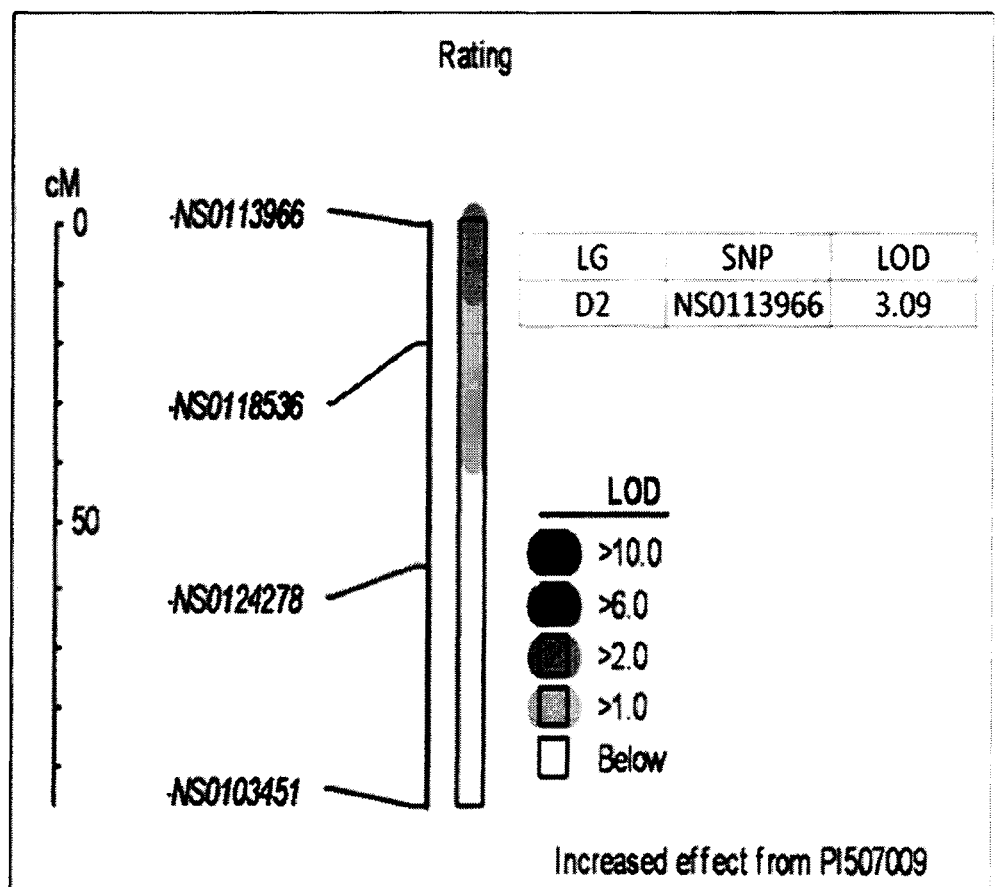
FIG. 3 depicts the positions of ASR locus 16 on linkage group D2. To the right is the legend for the LOD plot for the population. The gray bar indicates the confidence interval for the position of NS0113966 (LOD>2).

The ASR resistance locus 16 discovered in PI507009 and mapped to linkage group D2 of the public soybean genetic linkage map (FIG. 3). Two SNP markers, NS0118536 (R Sq>0.050) and NS0113966 (R Sq>0.150) were found to be in linkage disequilibria with the ASR resistance locus 16 disease phenotypic response, and therefore associated with ASR resistance locus 16. Both SNP markers were identified as being useful in monitoring the introgression of ASR resistance locus 16. SNP marker NS0113966 corresponds to SEQ ID NO: 7; and NS0118536 corresponds to SEQ ID NO: 8. Table 1 lists the SNP markers, their chromosome positions, SNP positions, the resistance allele and the SEQ ID number for the resistance allele for each SNP.

Example 2

Exemplary Marker Assays for Detecting ASR Resistance

In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means. Exemplary primers and probes for amplifying and detecting genomic regions associated with ASR resistance are given in Table 2.

Example 3

Oligonucleotide Hybridization Probes Useful for Detecting Soybean Plants with ASR Resistance Loci Oligonucleotides can also be used to detect or type the polymorphisms associated with the ASR resistance locus disclosed herein using hybridization-based SNP detection methods. Exemplary oligonucleotides capable of hybridizing to isolated nucleic acid sequences which include the polymorphism are provided. It is within the skill of the art to design assays with experimentally determined stringency to discriminate between the allelic states of the polymorphisms presented herein. Exemplary assays include Southern blots, Northern blots, microarrays, in situ hybridization, and other methods of polymorphism detection based on hybridization. Exemplary oligonucleotides for use in hybridization-based SNP detection are provided in Table 3. These oligonucleotides can be detectably labeled with radioactive labels, fluorophores, or other chemiluminescent means to facilitate detection of hybridization to samples of genomic or amplified nucleic acids derived from one or more soybean plants using methods known in the art.

TABLE 1

Listing of SNP markers for ASR resistance loci 14, 15 and 16 with the resistance and susceptibility allele for each marker indicated. The resistance allele corresponds to the 35 base pair nucleic acid sequence that includes the polymorphism associated with ASR resistance.

| Marker | Linkage Group | Chromosome Position | ASR resistance locus | SEQ ID NO. | SNP position | Favorable parent | Resistance allele | Susceptibility allele | SEQ ID NO. of resistance allele |
|---|---|---|---|---|---|---|---|---|---|
| NS0095012 | G | 85.2 | 14 | 1 | 99 | PI291309C | G | T | 73 |
| NS0119675 | G | 113.0 | 14 | 2 | 53 | PI291309C | A | T | 74 |
| NS0102630 | G | 132.1 | 14 | 3 | 186 | PI291309C | C | A | 75 |
| NS0093385 | C2 | 129.4 | 15 | 4 | 109 | PI507009 | T | C | 76 |
| NS0118716 | C2 | 149.9 | 15 | 5 | 366 | PI507009 | C | T | 77 |
| NS0127833 | C2 | 171.2 | 15 | 6 | 57 | PI507009 | T | C | 78 |
| NS0113966 | D2 | 49.6 | 16 | 7 | 332 | PI507009 | G | A | 79 |
| NS0118536 | D2 | 75.5 | 16 | 8 | 286 | PI507009 | C | T | 80 |

TABLE 2

Exemplary assays for detecting ASR resistance.

| Marker | Marker SEQ ID NO | SNP Position | SEQ ID NO Forward Primer | SEQ ID NO Reverse Primer | SEQ ID NO Probe 1 | SEQ ID NO Probe 2 |
|---|---|---|---|---|---|---|
| NS0095012 | 1 | 99 | 9 | 10 | 25 | 26 |
| NS0119675 | 2 | 53 | 11 | 12 | 27 | 28 |
| NS0102630 | 3 | 186 | 13 | 14 | 29 | 30 |
| NS0093385 | 4 | 109 | 15 | 16 | 31 | 32 |
| NS0118716 | 5 | 366 | 17 | 18 | 33 | 34 |
| NS0127833 | 6 | 57 | 19 | 20 | 35 | 36 |
| NS0113966 | 7 | 332 | 21 | 22 | 37 | 38 |
| NS0118536 | 8 | 286 | 23 | 24 | 39 | 40 |

TABLE 3

Oligonucleotide Hybridization Probes

| Marker | Marker SEQ ID NO | SNP Position | Hybridization Probe | Probe SEQ ID NO | Allele Detected |
|---|---|---|---|---|---|
| NS0095012 | 1 | 99 | CTGGCTTT GTGGGGCA | 41 | Resistance |
| NS0095012 | 1 | 99 | CTGGCTTT TTGGGGCA | 42 | Susceptibility |
| NS0119675 | 2 | 53 | TCCTCTGA ACATACTG | 43 | Resistance |
| NS0119675 | 2 | 53 | TCCTCTGA TCATACTG | 44 | Susceptibility |
| NS0102630 | 3 | 186 | CAAGTGAT CTTGAGAG | 45 | Resistance |
| NS0102630 | 3 | 186 | CAAGTGAT ATTGAGAG | 46 | Susceptibility |
| NS0093385 | 4 | 109 | CTCACCTT TAGTTACA | 47 | Resistance |
| NS0093385 | 4 | 109 | CTCACCTT CAGTTACA | 48 | Susceptibility |
| NS0118716 | 5 | 366 | CTACAGAC CCTATGTG | 49 | Resistance |

TABLE 3-continued

Oligonucleotide Hybridization Probes

| Marker | Marker SEQ ID NO | SNP Position | Hybridization Probe | Probe SEQ ID NO | Allele Detected |
|---|---|---|---|---|---|
| NS0118716 | 5 | 366 | CTACAGAC TCTATGTG | 50 | Susceptibility |
| NS0127833 | 6 | 57 | CATGCTAG TGTATCAG | 51 | Resistance |
| NS0127833 | 6 | 57 | CATGCTAG CGTATCAG | 52 | Susceptibility |
| NS0113966 | 7 | 332 | GATGCATA GAGATTGA | 53 | Resistance |
| NS0113966 | 7 | 332 | GATGCATA AAGATTGA | 54 | Susceptibility |
| NS0118536 | 8 | 286 | ATACTAAA CGGCTGGT | 55 | Resistance |
| NS0118536 | 8 | 286 | ATACTAAA TGGCTGGT | 56 | Susceptibility |

Example 4

Oligonucleotide Probes Useful for Detecting Soybean Plants with ASR Resistance Loci by Single Base Extension Methods Oligonucleotides can also be used to detect or type the polymorphisms associated with ASR resistance disclosed herein by single base extension (SBE)-based SNP detection methods. Exemplary oligonucleotides for use in SBE-based SNP detection are provided in Table 3. SBE methods are based on extension of a nucleotide primer that is hybridized to sequences adjacent to a polymorphism to incorporate a detectable nucleotide residue upon extension of the primer. It is also anticipated that the SBE method can use three synthetic oligonucleotides. Two of the oligonucleotides serve as PCR primers and are complementary to the sequence of the locus which flanks a region containing the polymorphism to be assayed. Exemplary PCR primers that can be used to type polymorphisms disclosed in this invention are provided in Table 4 in the columns labeled "Forward Primer SEQ ID" and "Reverse Primer SEQ ID." Following amplification of the region containing the polymorphism, the PCR product is hybridized with an extension primer which anneals to the amplified DNA adjacent to the polymorphism. DNA polymerase and two differentially labeled dideoxynucleoside triphosphates are then provided. If the polymorphism is present on the template, one of the labeled dideoxynucleoside triphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

TABLE 4

Probes (extension primers) for Single Base Extension (SBE) assays.

| Marker | Marker SEQ ID NO | SNP Position | Probe (SBE) | Resistance allele | SBE Probe SEQ ID NO | Forward Primer SEQ ID NO | Reverse Primer SEQ ID NO |
|---|---|---|---|---|---|---|---|
| NS0095012 | 1 | 99 | TGTCAAATGCTGGCTTT | G | 57 | 9 | 10 |
| NS0095012 | 1 | 99 | AATTGGAATTTGCCCCA | C | 58 | 9 | 10 |
| NS0119675 | 2 | 53 | ATTACCAAATCCTCTGA | A | 59 | 11 | 12 |
| NS0119675 | 2 | 53 | TTAGAAGACCCAGTATG | T | 60 | 11 | 12 |
| NS0102630 | 3 | 186 | AGAGAAACTCAAGTGAT | C | 61 | 13 | 14 |
| NS0102630 | 3 | 186 | CACATACTCACTCTCAA | G | 62 | 13 | 14 |
| NS0093385 | 4 | 109 | ATTTAAAGACTCACCTT | T | 63 | 15 | 16 |
| NS0093385 | 4 | 109 | TTAAACTTGGTGTAACT | T | 64 | 15 | 16 |
| NS0118716 | 5 | 366 | TGACACTAGCTACAGAC | C | 65 | 17 | 18 |
| NS0118716 | 5 | 366 | ATTCTCACCTCACATAG | C | 66 | 17 | 18 |
| NS0127833 | 6 | 57 | ACCATGAGTCATGCTAG | T | 67 | 19 | 20 |
| NS0127833 | 6 | 57 | TTGAATTCCCTGATAC | T | 68 | 19 | 20 |
| NS0113966 | 7 | 332 | GTTCTTGAAGATGCATA | G | 69 | 21 | 22 |

TABLE 4-continued

Probes (extension primers) for Single Base Extension (SBE) assays.

| Marker | Marker SEQ ID NO | SNP Position | Probe (SBE) | Resistance allele | SBE Probe SEQ ID NO | Forward Primer SEQ ID NO | Reverse Primer SEQ ID NO |
|---|---|---|---|---|---|---|---|
| NS0113966 | 7 | 332 | CATCAACTACTCAATCT | G | 70 | 21 | 22 |
| NS0118536 | 8 | 286 | CAGAACAAAATACTAAA | C | 71 | 23 | 24 |
| NS0118536 | 8 | 286 | AAATTCCAGAACCAGCC | C | 72 | 23 | 24 |

Example 5

Incorporation of Markers into Screening of Candidate Soybean Lines

ASR is an aggressive pathogen and can evolve rapidly. ASR has overcome single resistance genes in South America and China Therefore, it is critical to stack resistance genes to provide broader more durable resistance. Novel resistance sources must be identified to facilitate stacking resistance loci. Numerous resistance PIs have been identified from over 5000 PIs from Japan, China, Vietnam, and Indonesia screened for ASR resistance by the detached leaf technique (U.S. application Ser. No. 11/805,667). The resistant germplasm must be prioritized for further characterization, such as molecular mapping To prioritize research efforts, novel resistant PIs screened for previously identified ASR resistance loci Rpp1, Rpp2, Rpp3 and Rpp4. Utilizing the diagnostic SNPs associated with the Rpp genes (U.S. application Ser. No. 11/805,667), DNA from leaf tissue of novel resistant PIs were analyzed to determine if these PIs contain haplotypes corresponding to Rpp1, Rpp2, Rpp3 and Rpp4. PIs with a haplotype which does not correlate with Rpp1, Rpp2, Rpp3 and Rpp4, and which have a favorable phenotype with respect to any Phakopsora isolate or any geography are given priority for population development and molecular mapping of the resistant loci. In addition, for specific geographies or specific Phakopsora isolates, PIs with a haplotype matching that of a characterized Rpp source associated with an uncharacterized region having a favorable phenotype, are likewise given priority for population development and mapping of the uncharacterized resistance determinant(s). Rapid screening for known haplotypes thus has the advantage of minimizing effort expended on the bioassay of candidates likely to comprise just previously characterized loci and allowing effort to be focused on novel candidates not previously characterized. One of skill in the art will immediately see that the haplotype screening process can include any known haplotype associated with a characterized resistance phenotype and not linked to an uncharacterized resistance region, including those haplotypes comprising markers disclosed in the present invention.

Example 6

Cross-Testing of Germplasm for Differential Responses to U.S. and Ex-U.S. Races of Phakopsora The ASR resistance loci and markers of the present invention are useful for cross-testing haplotypes for differential associations with resistance to different races of Phakopsora. The previously described Rpp resistance genes confer less resistance against South American isolates of Phakopsora as compared to North American isolates; however, LG C2 appears to have a favorable haplotype near NS0137477 (AA, SEQ ID 90 in U.S. application Ser. No. 11/805,667) which confirms tolerance to South American Phakopsora isolates. Therefore, PIs which have the favorable allele at this SNP or contain rare SNP alleles in the distal region of LG C2 are given priority for international testing in Brazil and other geographies with ASR disease pressure around the world. Additionally, PIs found to be resistant to North American isolates of Phakopsora are given priority for international testing over PIs lacking resistance to North American isolates of Phakopsora, although all are eventually tested to ensure that a possible source of resistance, tolerance or immunity to any ex-U.S. isolates of Phakopsora is not missed. As international testing of these PIs is completed, resistance profiles with respect to Phakopsora isolates around the world are developed, and molecular markers and haplotypes of the present invention provide the basis for describing the importance of the corresponding PIs as well as related PIs on a regional basis. PIs which have favorable phenotypes in a given locale are utilized in population development and mapping efforts to identify molecular markers associated with the resistance phenotype.

Example 7

Accumulation of Multiple Resistance Loci into Soybean Germplasm

In other aspects, the methods and compositions of the present invention are useful for the accumulation of multiple resistance loci into individual lines. In a preferred embodiment of the invention, populations are generated comprising one or more resistance loci from novel sources of ASR resistance that are introgressed in preferred genetic backgrounds for testing in both North America and South America. Once ASR-resistant populations have been developed, with ASR resistance loci fixed and agronomically elite genetics selected for via backcrossing, near isogenic lines (NILs) are evaluated domestically and internationally. Simultaneously, NILs with unique ASR resistance haplotypes are intercrossed and/or forward bred to stack two or more favorable ASR alleles. These single and stacked combinations enable the development of customized and durable ASR-resistant varieties for a given geographic region. Single NILs also serve as differentials when Phakopsora isolates change in a given region and provide insight to which resistance source(s) should be deployed next. The use of markers of the present invention towards these ends will be obvious to one skilled in the art. For example, two resistant lines (e.g., PI291309C and PI507009) or lines with ASR resistance comprising ASR resistance locus 14, ASR resistance locus 15, and ASR resistance locus 16, are the donor parents for three ASR resistance loci, selected from the group comprising ASR resistance locus 14, ASR resistance locus 15 and ASR resistance locus 16, and monitored by screening with the molecular markers denoted by SEQ IDS: 1-8 and selecting for lines carrying the resistance allele for one or more of said molecular markers, representing one or more of said ASR resistance loci, wherein the SNP marker for ASR resistance locus 14 is selected from the group consisting of NS0095012 (SEQ ID 1), NS0119675 (SEQ ID 2) and NS0102630 (SEQ ID 3) and the resistance allele for each marker is indicated in Table 3. Also, one or more SNP markers for ASR resistance locus 15 is selected from the group consisting of NS0093385 (SEQ ID 4), NS0118716 (SEQ ID 5) and NS0127833 (SEQ ID 6) and the resistance allele for each marker is indicated in Table 3. Also, one or more SNP markers for ASR resistance locus 16 is selected from the group consisting of NS0113966 (SEQ ID 7) and NS0118536 (SEQ ID 8) and the resistance allele for each marker is indicated in Table 3. It will be evident to one skilled in the art that such methods can moreover be used to combine one or more resistance loci of the present invention with one or more resistance loci known to the art.

The introgression of one or more resistance loci is achieved via repeated backcrossing to a recurrent parent accompanied by selection to retain one or more ASR resistance loci from the donor parent using the above-described markers. This backcross procedure is implemented at any stage in varietal development and occurs in conjunction with breeding for superior agronomic characteristics or one or more traits of interest, including transgenic and nontransgenic traits.

Alternatively, a forward breeding approach is employed wherein one or more ASR resistance loci can be monitored for successful introgression following a cross with a susceptible parent with subsequent generations genotyped for one or more ASR resistance loci and for one or more additional traits of interest, including transgenic and non-transgenic traits.

All patent and non-patent documents cited in this specification are incorporated herein by reference in their entireties, to the same extent as if each individual was specifically and individually indicated to be incorporated by reference. Documents cited herein as being available from the World Wide Web at certain internet addresses are also incorporated herein by reference in their entireties. Certain biological sequences referenced herein by their "NCBI Accession Number" can be accessed through the National Center of Biotechnology Information on the World Wide Web at ncbi.nlm.nih.gov.

As various modifications could be made in the methods herein described and illustrated without departing from the scope of the invention, it is intended that all matter contained in the foregoing description or shown in the accompanying drawings shall be interpreted as illustrative rather than limiting. Having illustrated and described the principles of the present invention, it should be apparent to persons skilled in the art that the invention can be modified in arrangement and detail without departing from such principles. All such modifications in arrangement and detail are considered to fall within the spirit and scope of the appended claims. Thus, the breadth and scope of the present invention should not be limited by any of the above-described exemplary embodiments, but should be defined only in accordance with the following claims appended hereto and their equivalents.

What is claimed is:

1. A method of creating a population of soybean plants comprising Asian Soybean Rust (ASR) resistance locus 15, the method comprising the steps of:

genotyping a first population of soybean plants at a marker locus within 10 centimorgans or less from a SNP marker selected from the group consisting of NS0093385, NS0118716, and NS0127833, said population containing said ASR resistance locus 15;

selecting from said first population one or more identified soybean plants containing said ASR resistance locus 15; and producing from said selected soybean plants a second population, thereby creating a population of soybean plants comprising said ASR resistance locus 15;

wherein ASR resistance locus 15 is identified by one or more of the markers selected from the group consisting of NS0093385, NS0118716, and NS0127833, wherein a resistance allele of each of said markers NS0093385, NS0118716, and NS0127833, comprises SEQ ID NOs: 76, 77, and 78, respectively.

2. The method of claim 1, wherein said method produces an ASR resistant elite soybean plant.

3. The method of claim 1, wherein said molecular marker is detected using an assay selected from the group consisting of single base extension (SBE), allele-specific primer extension sequencing (ASPE), DNA sequencing, RNA sequencing, microarray-based analyses, universal PCR, allele specific extension, hybridization, mass spectrometry, ligation, extension-ligation, and Flap Endonuclease-mediated assays.

4. The method of claim 1, wherein said ASR locus 15 is obtainable from PI507009.

5. The method of claim 1, wherein said ASR resistance is resistance to *Phakopsora pachyrhizi* or *Phakopsora meibomiae*.

6. The method of claim 1, wherein said progeny plant exhibits at least partial resistance to at least one race of an ASR-inducing fungus.

7. The method of claim 1, wherein the ASR resistance of said progeny plant is derived from ASR resistance locus 15.

* * * * *

SEQUENCE LISTING

```
<160> NUMBER OF SEQ ID NOS: 80

<210> SEQ ID NO 1
<211> LENGTH: 466
<212> TYPE: DNA
<213> ORGANISM: Glycine max

<400> SEQUENCE: 1
aattgaattt ggctcacaat gacttcggtt ctgtgattcc ttccaagttt ggcttgctga      60
aaaatttgag gtacttgaat ttgtcaaatg ctggcttttt ggggcaaatt ccaattgaga     120
ttggtcttct aacaaagatg gctactcttg acttatctac ttcgtttact ttagagcata     180
ctctaaaact tgagaagcca aacataggag tgcttatgaa gaacctcaca gaaatcacag     240
aactctacct agatggtgta atggtatctg ctactggaaa ggagtggtct catgcattat     300
cttcaatgca aaagcttcaa gttttgagca tgtcatcctg taacctctca ggaccaattg     360
attcttcact gtcaaagctt aagtctctct cagtgattca attgaatttg aacaatgtgt     420
caagtccagt accagaatcc ttggcaaatc tctcaaattt gaccac                    466

<210> SEQ ID NO 2
<211> LENGTH: 733
<212> TYPE: DNA
<213> ORGANISM: Glycine max

<400> SEQUENCE: 2
```

```
tgagaacact gccaaagctt tttggcatct ttcctattac caaatcctct gaacatactg    60
ggtcttctaa aggtccttgg gacaaaccag tgtttcacca aaaacactga acaagttatt   120
ccaaagatgc tggtgggcaa tgcaaaaaca atgagaaaaa agattcagaa ctcatttcga   180
tattgaacat tgtgtcacca tgatgttgtg ttgactttta cattttgacc tatgtttccc   240
atttgaaatt tcttttttctt ttctgcgtgg gtaattaaca ttatagtgat agtaccctct   300
```

```
ttttgtaatt tcagttgatt ctgtttggtt gttaagttac tccatttaat tgtataatct   360
tgttgatgga cattattaaa catcctaaat ttcatttttt ttagtaatct gttgcttata   420 cttttttacag gtgaaaaatg tcatgtaact gatgcttcaa atcctgcttt aagttaccaa   480
gagactatgg agccttctgt atctaaagaa acacctaatt cagggaaaac tgatatgcaa   540
cttgagagtc agatatttag taataaagta gaaagtatta cagatctgc tgctactgac    600 atgccagagc ctgaaaagtt gctctcagct taccaacatg atggtgaagc aaatgatttg   660
ctgatggcat ctactcctga caatcagggt gcaactgaag gccatacagg tgctgcaggc   720
atgcaagctg gcc                                                      733
```

<210> SEQ ID NO 3
<211> LENGTH: 941
<212> TYPE: DNA
<213> ORGANISM: Glycine max

<400> SEQUENCE: 3

```
caagcttgtt gcctgcagaa aaagcacatg ggatagttgt taatagtttt gaagagttgg    60
aagcagaata tgttgaagag tgtcaaagat ttacggacca tagggtatgg tgtgttgggc   120
ctgtgtcgct gtcaaataag gatgacaagg acaaggctat gagaagtaag agaaactcaa   180
gtgatattga gagtgagtat gtgaagtggc ttgattcatg gcctccgagg tcagtgattt   240
atgtttgcct tggtagccta aaccgtgcaa cgccagagca gttgatagag ctcgggttag   300
gattggaagc gacaaaaagg ccattcattt gggtgcttag aggtgcatat ggaagagagg   360
agatggagaa gtggctgttg aagatgggt ttgaagagag ggtgaaaggg agagggcttt   420
tgatcaaggg ttgggtgcca caagtgttga tcttatcaca tagagcaata ggagcgttca   480
tgacacattg cggatggaat tccacactcg aagggatttg tgctggcgtg ccgttggtaa   540
cttttcctct gtttgctgag cagttcatca atgagaaact tgtacaagtg gtgaagattg   600
gcgtgagtgt gggagctgaa tctgttgttc acttgggtga agaagataag tctcgggttc   660
aggtgaccag agaaaatgtt ctggattcta ttgaaaggta atgggagaat ggccaaaaaa   720
aaaaaaaata taggaaaggg ctttaaagta ttccgccatt ggcagggaaa gcaaaaaaa    780 aagtgggttt ttttctctcac atggtcctac tcattgggcc atataccttt ggagggttaa   840
ccaagtttaa ccagggttct attttttgtt ttcaacacca attgcttttc tcaagggtca   900
accttaaacc caatttgtct tccgaaagaa tttttttttt a                       941
```

<210> SEQ ID NO 4
<211> LENGTH: 435
<212> TYPE: DNA
<213> ORGANISM: Glycine max

<400> SEQUENCE: 4

```
aggcatcgga agatgagaag actgatgccc caaaagcaat tgagagtaca ccccagtcga    60 cacccccagtc tacttctgga attgaggatt tatttaaaga ctcacccttta gttacaccaa   120 gtttaactcc agaaaaacca caaaaagatc taaaaaatga tatcatgagc ctctttgaga   180
```

```
aggtatgtgc cagtgcttca ataggtttgt ttaaggctga gttacttctt tgagtttata    240
tatatatata tggttagaaa tgcttttaa aatatacaca ttctatattg ttgacatttc     300
ctccttgccc gatgtgagtt attatccaag acaccaaaac aagtgaattt agttgtcgat    360
cgatctctat ccttagatgg gttttatgt tttggtatgt gaataagatt ttacctgacc    420
cagtaaattg gacat                                                     435
```

<210> SEQ ID NO 5
<211> LENGTH: 431
<212> TYPE: DNA
<213> ORGANISM: Glycine max

<400> SEQUENCE: 5

```
ctttccttgc tggtttggct gcatcaggtg tactaacgtc tgctttgagg ttaattacaa     60
aagcagcatt tgagaaaact aagaacggtc ttcgcaaagg agccagtaag ttcagctctc    120
cagagcttaa gacatttgat aattcagagt ttagccgcat tcatgtttaa catagaaaat    180
tgaaaaaaaa aatatttagc ttatgcaatt gtttaactag cctttatttc tattttttca    240
atgtgtcaga aacaagtttt caaattgatt tttaactctt ttcatacaac tcatgaagat    300
atgaggttta ttgaagattg tggaattaat atgcttttaa taagatattg acactagcta    360
cagaccctat gtgaggtgag aatcctgtgg tttatgttgt agacttcacc tagtagaata    420
agactttgtt a                                                         431
```

<210> SEQ ID NO 6
<211> LENGTH: 1166
<212> TYPE: DNA
<213> ORGANISM: Glycine max

<400> SEQUENCE: 6

```
tctgaaacaa agaaagctgt gccaattgac atagatctga ccatgagtca tgctagcgta     60
tcagggaaat tcaatactca tgcaacaaat ggcaaagaga ttgaagtaat tgatttagaa    120
aatgatgatt ccattcaaga agagaagtca atcgacaata tggatagaaa gtacgttttt    180
cctgcttcct tcccccctgg atattttatg ttatcttttt taagcgttct tttatccaat    240
ctctcaaatt tagtgtttgt taggatctaa tttatctatt ttttttatcc ttgctttcag    300
ttacttagtg aaaatatcag ctggagcata gtttttaaa cacccttcat ttacttgcca    360
ctctcttcct aatatgttgt cttgaaatca caggacagag actatgtttc ctggccttga    420 aggttttct agccatgctc aaaatgctgc tgacatgcat gatgttcagg atggatatgg    480
gcttatgata tcagagttgc ttgggccaga tttccctaac tgttcttcag tacctggtga    540
cataaactct gtgcacaatg aaatgggcct tcaaagtgga acggtacaat gctaccttca    600
aattgagata tattttgatg catgtccttt taatataacc tttgctgact tgattgttgc    660
tgcatgcctt tataatcaac aatgaaatga ttctttattc tgagaagatt tttcttaata    720
atcataattg atgattttct cataatttca ttcttttcgt ttcagggggac acttgctgag    780 gatgattcca tatatatgtc gcttggagaa ttaagtatga cagatttta ttaatggttt     840 gttttcttat ttgttttttt ttttttttgc acagcaaaaa tcgatataga attttatata    900
taatgaagta ctaggtgtac tgcatacagg ataaagagta caaggcaaaa ttgcctaacc    960
catctgaaaa ttcaagata acattagctg aagccaaaaa gaatcaaccc ctaagacaac     1020
tcctccctca aactagtgga ccattgatta aaatgaatat ggaaatcttt gtccatacat    1080
```

```
tttaaccagg cccatgaatg gaataaagct tcatccatga cttatttgtt aagtgtacct   1140
gtgattcatg ttagttgata tttgat                                       1166

<210> SEQ ID NO 7
<211> LENGTH: 807
<212> TYPE: DNA
<213> ORGANISM: Glycine max

<400> SEQUENCE: 7
cagcttgcat gcctgcagat ttgtcataat ttagcatttt ttttcttttg aaacattcca     60
atacctttct ttcaaatcat tacctaaaga ggtaaaataa tgattgaaac aactgtgaac    120
aaattgttcc taatggctaa agaggcaag acaaagtcat ctaatacagt tttgtggatg     180
aataaaattg acaaggaact tgaccatggc agaagtattt gtaagcaaag tatttcatct    240
tgaaattagc aaatgtaagt tgtgtgagga tctttagaga ccaaaatcga gttaaacttt    300
tggagccaat ttcggttctt gaagatgcat agagattgag tagttgatgt gaaaagatga    360
agcggaatgg aaaaaatttt aaaaaatgag agaaaaattg aggggagaat gtgttcattg    420
ggcaaccgtg aagaaaaaac ttgatctaca cgatattatt tcagacactc aattgccata    480
attaaattta agggtttaaa atctcagtaa tacctgaaag attaaaaata caattaaacc    540
tgaaaaatat ggctcacatt ttgagaatgg gggagatatg tcaaatgaag tataaaccaa    600
gttatttatt gacaggcttg tatacaaagt gatttagatc accggactat caacaaaata    660
actcattctc caattacttt tatatagatc ttgtagtgct gtttcgctat agcaagaag    720 aaaaaaaaag gaaacaagga gagaaaatga agaaatgaag caaagattat agaaaaataa    780
agaaatggga gagagataga gagacta                                       807

<210> SEQ ID NO 8
<211> LENGTH: 467
<212> TYPE: DNA
<213> ORGANISM: Glycine max

<400> SEQUENCE: 8
tggatgccag aagaatttga acagcatcaa agcaaaggta acaggatct aggtacttgg     60 atgagccctt tattttcaaa atccaaccac atcctctttt agccgtctcc atcttaaaag    120
taacaaaata tattcatta atttaaagca taacctcttc aaaaaaaaat taagcatag     180 aaaaatatgt tcaagaccca atcactgagg caaagtgtgc taagcccagt ctgctacaca    240
tgtagggtta gctacattag agcctaacca gaacaaaata ctaaacggct ggttctggaa    300
tttgatcaat tataatggca ttcagaaaaa aaaattgttt tagaactagt aaaaatgtaa    360
atagcttttt tcgtatgctc aatttaaccc tgctccatga caataaccgt aaatatttt    420 tttgagtaaa aaaccgaatg catgtgagaa agtgatatga gcgaata                 467

<210> SEQ ID NO 9
<211> LENGTH: 26
<212> TYPE: DNA
<213> ORGANISM: Artificial sequence
<220> FEATURE:
<223> OTHER INFORMATION: Description of artificial sequence: synthetic
      primer

<400> SEQUENCE: 9
ttgctgaaaa atttgaggta cttgaa                                          26

<210> SEQ ID NO 10
```

```
<211> LENGTH: 24
<212> TYPE: DNA
<213> ORGANISM: Artificial sequence
<220> FEATURE:
<223> OTHER INFORMATION: Description of artificial sequence: synthetic
      primer

<400> SEQUENCE: 10
agaccaatct caattggaat ttgc                                           24

<210> SEQ ID NO 11
<211> LENGTH: 25
<212> TYPE: DNA
<213> ORGANISM: Artificial sequence
<220> FEATURE:
<223> OTHER INFORMATION: Description of artificial sequence: synthetic
      primer

<400> SEQUENCE: 11 cttttggca tctttcctat tacca                                           25

<210> SEQ ID NO 12
<211> LENGTH: 24
<212> TYPE: DNA
<213> ORGANISM: Artificial sequence
<220> FEATURE:
<223> OTHER INFORMATION: Description of artificial sequence: synthetic
      primer

<400> SEQUENCE: 12
gtttgtccca aggacctta gaag                                            24

<210> SEQ ID NO 13
<211> LENGTH: 27
<212> TYPE: DNA
<213> ORGANISM: Artificial sequence
<220> FEATURE:
<223> OTHER INFORMATION: Description of artificial sequence: synthetic
      primer

<400> SEQUENCE: 13
acaaggacaa ggctatgaga agtaaga                                        27

<210> SEQ ID NO 14
<211> LENGTH: 20
<212> TYPE: DNA
<213> ORGANISM: Artificial sequence
<220> FEATURE:
<223> OTHER INFORMATION: Description of artificial sequence: synthetic
      primer

<400> SEQUENCE: 14
ggccatgaat caagccactt                                                20

<210> SEQ ID NO 15
<211> LENGTH: 30
<212> TYPE: DNA
<213> ORGANISM: Artificial sequence
<220> FEATURE:
<223> OTHER INFORMATION: Description of artificial sequence: synthetic
      primer

<400> SEQUENCE: 15
acttctggaa ttgaggattt atttaaagac                                     30

<210> SEQ ID NO 16
<211> LENGTH: 27
```

```
<212> TYPE: DNA
<213> ORGANISM: Artificial sequence
<220> FEATURE:
<223> OTHER INFORMATION: Description of artificial sequence: synthetic
      primer

<400> SEQUENCE: 16 cttttgtgg tttttctgga gttaaac                                           27

<210> SEQ ID NO 17
<211> LENGTH: 33
<212> TYPE: DNA
<213> ORGANISM: Artificial sequence
<220> FEATURE:
<223> OTHER INFORMATION: Description of artificial sequence: synthetic
      primer

<400> SEQUENCE: 17
tggaattaat atgcttttaa taagatattg aca                                   33

<210> SEQ ID NO 18
<211> LENGTH: 28
<212> TYPE: DNA
<213> ORGANISM: Artificial sequence
<220> FEATURE:
<223> OTHER INFORMATION: Description of artificial sequence: synthetic
      primer

<400> SEQUENCE: 18
gaagtctaca acataaacca caggattc                                         28

<210> SEQ ID NO 19
<211> LENGTH: 25
<212> TYPE: DNA
<213> ORGANISM: Artificial sequence
<220> FEATURE:
<223> OTHER INFORMATION: Description of artificial sequence: synthetic
      primer

<400> SEQUENCE: 19
ccaattgaca tagatctgac catga                                            25

<210> SEQ ID NO 20
<211> LENGTH: 24
<212> TYPE: DNA
<213> ORGANISM: Artificial sequence
<220> FEATURE:
<223> OTHER INFORMATION: Description of artificial sequence: synthetic
      primer

<400> SEQUENCE: 20
gccatttgtt gcatgagtat tgaa                                             24

<210> SEQ ID NO 21
<211> LENGTH: 20
<212> TYPE: DNA
<213> ORGANISM: Artificial sequence
<220> FEATURE:
<223> OTHER INFORMATION: Description of artificial sequence: synthetic
      primer

<400> SEQUENCE: 21
ggagccaatt tcggttcttg                                                  20

<210> SEQ ID NO 22
<211> LENGTH: 25
<212> TYPE: DNA
```

```
<213> ORGANISM: Artificial sequence
<220> FEATURE:
<223> OTHER INFORMATION: Description of artificial sequence: synthetic
      primer

<400> SEQUENCE: 22
cgcttcatct tttcacatca actac                                          25

<210> SEQ ID NO 23
<211> LENGTH: 27
<212> TYPE: DNA
<213> ORGANISM: Artificial sequence
<220> FEATURE:
<223> OTHER INFORMATION: Description of artificial sequence: synthetic
      primer

<400> SEQUENCE: 23
agctacatta gagcctaacc agaacaa                                        27

<210> SEQ ID NO 24
<211> LENGTH: 27
<212> TYPE: DNA
<213> ORGANISM: Artificial sequence
<220> FEATURE:
<223> OTHER INFORMATION: Description of artificial sequence: synthetic
      primer

<400> SEQUENCE: 24
ttctgaatgc cattataatt gatcaaa                                        27

<210> SEQ ID NO 25
<211> LENGTH: 15
<212> TYPE: DNA
<213> ORGANISM: Artificial sequence
<220> FEATURE:
<223> OTHER INFORMATION: Description of artificial sequence: synthetic
      probe

<400> SEQUENCE: 25
tgctggcttt gtggg                                                     15

<210> SEQ ID NO 26
<211> LENGTH: 13
<212> TYPE: DNA
<213> ORGANISM: Artificial sequence
<220> FEATURE:
<223> OTHER INFORMATION: Description of artificial sequence: synthetic
      probe

<400> SEQUENCE: 26
tgctggcttt ttg                                                       13

<210> SEQ ID NO 27
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 27
cctctgaaca tactgg                                                    16

<210> SEQ ID NO 28
<211> LENGTH: 16
<212> TYPE: DNA
<213> ORGANISM: Artificial sequence
```

```
<220> FEATURE:
<223> OTHER INFORMATION: Description of artificial sequence: synthetic
      probe

<400> SEQUENCE: 28
cctctgatca tactgg                                                       16

<210> SEQ ID NO 29
<211> LENGTH: 15
<212> TYPE: DNA
<213> ORGANISM: Artificial sequence
<220> FEATURE:
<223> OTHER INFORMATION: Description of artificial sequence: synthetic
      probe

<400> SEQUENCE: 29
ctcactctca atatc                                                        15

<210> SEQ ID NO 30
<211> LENGTH: 15
<212> TYPE: DNA
<213> ORGANISM: Artificial sequence
<220> FEATURE:
<223> OTHER INFORMATION: Description of artificial sequence: synthetic
      probe

<400> SEQUENCE: 30
cactctcaag atcac                                                        15

<210> SEQ ID NO 31
<211> LENGTH: 18
<212> TYPE: DNA
<213> ORGANISM: Artificial sequence
<220> FEATURE:
<223> OTHER INFORMATION: Description of artificial sequence: synthetic
      probe

<400> SEQUENCE: 31
caccttcagt tacaccaa                                                     18

<210> SEQ ID NO 32
<211> LENGTH: 19
<212> TYPE: DNA
<213> ORGANISM: Artificial sequence
<220> FEATURE:
<223> OTHER INFORMATION: Description of artificial sequence: synthetic
      probe

<400> SEQUENCE: 32
tcacctttag ttacaccaa                                                    19

<210> SEQ ID NO 33
<211> LENGTH: 15
<212> TYPE: DNA
<213> ORGANISM: Artificial sequence
<220> FEATURE:
<223> OTHER INFORMATION: Description of artificial sequence: synthetic
      probe

<400> SEQUENCE: 33
cctcacatag ggtct                                                        15

<210> SEQ ID NO 34
<211> LENGTH: 16
<212> TYPE: DNA
<213> ORGANISM: Artificial sequence
<220> FEATURE:
```

```
<223> OTHER INFORMATION: Description of artificial sequence: synthetic
      probe

<400> SEQUENCE: 34
acctcacata gagtct                                                     16

<210> SEQ ID NO 35
<211> LENGTH: 18
<212> TYPE: DNA
<213> ORGANISM: Artificial sequence
<220> FEATURE:
<223> OTHER INFORMATION: Description of artificial sequence: synthetic
      probe

<400> SEQUENCE: 35
tttccctgat acgctagc                                                   18

<210> SEQ ID NO 36
<211> LENGTH: 17
<212> TYPE: DNA
<213> ORGANISM: Artificial sequence
<220> FEATURE:
<223> OTHER INFORMATION: Description of artificial sequence: synthetic
      probe

<400> SEQUENCE: 36
cctgatacac tagcatg                                                    17

<210> SEQ ID NO 37
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 37
agatgcataa agattg                                                     16

<210> SEQ ID NO 38
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 38
agatgcatag agattg                                                     16

<210> SEQ ID NO 39
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 39
ccagccgttt agtatt                                                     16

<210> SEQ ID NO 40
<211> LENGTH: 15
<212> TYPE: DNA
<213> ORGANISM: Artificial sequence
<220> FEATURE:
<223> OTHER INFORMATION: Description of artificial sequence: synthetic
``` probe

<400> SEQUENCE: 40
aaccagccat ttagt                                                         15

<210> SEQ ID NO 41
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 41
ctggctttgt ggggca                                                        16

<210> SEQ ID NO 42
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 42
ctggcttttt ggggca                                                        16

<210> SEQ ID NO 43
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 43
tcctctgaac atactg                                                        16

<210> SEQ ID NO 44
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 44
tcctctgatc atactg                                                        16

<210> SEQ ID NO 45
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 45
caagtgatct tgagag                                                        16

<210> SEQ ID NO 46
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 46
caagtgatat tgagag                                                    16

<210> SEQ ID NO 47
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 47
ctcaccttta gttaca                                                    16

<210> SEQ ID NO 48
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 48
ctcaccttca gttaca                                                    16

<210> SEQ ID NO 49
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 49
ctacagaccc tatgtg                                                    16

<210> SEQ ID NO 50
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 50
ctacagactc tatgtg                                                    16

<210> SEQ ID NO 51
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 51
catgctagtg tatcag                                                    16

<210> SEQ ID NO 52
<211> LENGTH: 16
<212> TYPE: DNA
<213> ORGANISM: Artificial sequence
<220> FEATURE:
<223> OTHER INFORMATION: Description of artificial sequence: synthetic
      probe

```
<400> SEQUENCE: 52
catgctagcg tatcag                                                    16

<210> SEQ ID NO 53
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 53
gatgcataga gattga                                                    16

<210> SEQ ID NO 54
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 54
gatgcataaa gattga                                                    16

<210> SEQ ID NO 55
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 55
atactaaacg gctggt                                                    16

<210> SEQ ID NO 56
<211> LENGTH: 16
<212> TYPE: DNA
<213> ORGANISM: Artificial sequence
<220> FEATURE:
<223> OTHER INFORMATION: Description of artificial sequence: synthetic
      probe

<400> SEQUENCE: 56
atactaaatg gctggt                                                    16

<210> SEQ ID NO 57
<211> LENGTH: 17
<212> TYPE: DNA
<213> ORGANISM: Artificial sequence
<220> FEATURE:
<223> OTHER INFORMATION: Description of artificial sequence: synthetic
      probe

<400> SEQUENCE: 57
tgtcaaatgc tggcttt                                                   17

<210> SEQ ID NO 58
<211> LENGTH: 17
<212> TYPE: DNA
<213> ORGANISM: Artificial sequence
<220> FEATURE:
<223> OTHER INFORMATION: Description of artificial sequence: synthetic
      probe

<400> SEQUENCE: 58
```
aattggaatt tgcccca                                                 17

<210> SEQ ID NO 59
<211> LENGTH: 17
<212> TYPE: DNA
<213> ORGANISM: Artificial sequence
<220> FEATURE:
<223> OTHER INFORMATION: Description of artificial sequence: synthetic
      probe

<400> SEQUENCE: 59
attaccaaat cctctga                                                 17

<210> SEQ ID NO 60
<211> LENGTH: 17
<212> TYPE: DNA
<213> ORGANISM: Artificial sequence
<220> FEATURE:
<223> OTHER INFORMATION: Description of artificial sequence: synthetic
      probe

<400> SEQUENCE: 60
ttagaagacc cagtatg                                                 17

<210> SEQ ID NO 61
<211> LENGTH: 17
<212> TYPE: DNA
<213> ORGANISM: Artificial sequence
<220> FEATURE:
<223> OTHER INFORMATION: Description of artificial sequence: synthetic
      probe

<400> SEQUENCE: 61
agagaaactc aagtgat                                                 17

<210> SEQ ID NO 62
<211> LENGTH: 17
<212> TYPE: DNA
<213> ORGANISM: Artificial sequence
<220> FEATURE:
<223> OTHER INFORMATION: Description of artificial sequence: synthetic
      probe

<400> SEQUENCE: 62
cacatactca ctctcaa                                                 17

<210> SEQ ID NO 63
<211> LENGTH: 17
<212> TYPE: DNA
<213> ORGANISM: Artificial sequence
<220> FEATURE:
<223> OTHER INFORMATION: Description of artificial sequence: synthetic
      probe

<400> SEQUENCE: 63
atttaaagac tcacctt                                                 17

<210> SEQ ID NO 64
<211> LENGTH: 17
<212> TYPE: DNA
<213> ORGANISM: Artificial sequence
<220> FEATURE:
<223> OTHER INFORMATION: Description of artificial sequence: synthetic
      probe

<400> SEQUENCE: 64

```
ttaaacttgg tgtaact                                                    17

<210> SEQ ID NO 65
<211> LENGTH: 17
<212> TYPE: DNA
<213> ORGANISM: Artificial sequence
<220> FEATURE:
<223> OTHER INFORMATION: Description of artificial sequence: synthetic
      probe

<400> SEQUENCE: 65
tgacactagc tacagac                                                    17

<210> SEQ ID NO 66
<211> LENGTH: 17
<212> TYPE: DNA
<213> ORGANISM: Artificial sequence
<220> FEATURE:
<223> OTHER INFORMATION: Description of artificial sequence: synthetic
      probe

<400> SEQUENCE: 66
attctcacct cacatag                                                    17

<210> SEQ ID NO 67
<211> LENGTH: 17
<212> TYPE: DNA
<213> ORGANISM: Artificial sequence
<220> FEATURE:
<223> OTHER INFORMATION: Description of artificial sequence: synthetic
      probe

<400> SEQUENCE: 67
accatgagtc atgctag                                                    17

<210> SEQ ID NO 68
<211> LENGTH: 17
<212> TYPE: DNA
<213> ORGANISM: Artificial sequence
<220> FEATURE:
<223> OTHER INFORMATION: Description of artificial sequence: synthetic
      probe

<400> SEQUENCE: 68
ttgaatttcc ctgatac                                                    17

<210> SEQ ID NO 69
<211> LENGTH: 17
<212> TYPE: DNA
<213> ORGANISM: Artificial sequence
<220> FEATURE:
<223> OTHER INFORMATION: Description of artificial sequence: synthetic
      probe

<400> SEQUENCE: 69
gttcttgaag atgcata                                                    17

<210> SEQ ID NO 70
<211> LENGTH: 17
<212> TYPE: DNA
<213> ORGANISM: Artificial sequence
<220> FEATURE:
<223> OTHER INFORMATION: Description of artificial sequence: synthetic
      probe

<400> SEQUENCE: 70
catcaactac tcaatct                                                    17
```

<210> SEQ ID NO 71
<211> LENGTH: 17
<212> TYPE: DNA
<213> ORGANISM: Artificial sequence
<220> FEATURE:
<223> OTHER INFORMATION: Description of artificial sequence: synthetic probe

<400> SEQUENCE: 71
cagaacaaaa tactaaa                                                17

<210> SEQ ID NO 72
<211> LENGTH: 17
<212> TYPE: DNA
<213> ORGANISM: Artificial sequence
<220> FEATURE:
<223> OTHER INFORMATION: Description of artificial sequence: synthetic probe

<400> SEQUENCE: 72
aaattccaga accagcc                                                17

<210> SEQ ID NO 73
<211> LENGTH: 35
<212> TYPE: DNA
<213> ORGANISM: Glycine max

<400> SEQUENCE: 73
tgtcaaatgc tggctttgtg gggcaaattc caatt                            35

<210> SEQ ID NO 74
<211> LENGTH: 35
<212> TYPE: DNA
<213> ORGANISM: Glycine max

<400> SEQUENCE: 74
attaccaaat cctctgaaca tactgggtct tctaa                            35

<210> SEQ ID NO 75
<211> LENGTH: 35
<212> TYPE: DNA
<213> ORGANISM: Glycine max

<400> SEQUENCE: 75
agagaaactc aagtgatctt gagagtgagt atgtg                            35

<210> SEQ ID NO 76
<211> LENGTH: 35
<212> TYPE: DNA
<213> ORGANISM: Glycine max

<400> SEQUENCE: 76
atttaaagac tcacctttag ttacaccaag tttaa                            35

<210> SEQ ID NO 77
<211> LENGTH: 35
<212> TYPE: DNA
<213> ORGANISM: Glycine max

<400> SEQUENCE: 77
tgacactagc tacagaccct atgtgaggtg agaat                            35

<210> SEQ ID NO 78

-continued

```
<211> LENGTH: 35
<212> TYPE: DNA
<213> ORGANISM: Glycine max

<400> SEQUENCE: 78
accatgagtc atgctagtgt atcagggaaa ttcaa                              35

<210> SEQ ID NO 79
<211> LENGTH: 35
<212> TYPE: DNA
<213> ORGANISM: Glycine max

<400> SEQUENCE: 79
gttcttgaag atgcatagag attgagtagt tgatg                              35

<210> SEQ ID NO 80
<211> LENGTH: 35
<212> TYPE: DNA
<213> ORGANISM: Glycine max

<400> SEQUENCE: 80
cagaacaaaa tactaaacgg ctggttctgg aattt                              35
```